United States Patent
Zeitlin et al.

(10) Patent No.: US 7,557,144 B1
(45) Date of Patent: Jul. 7, 2009

(54) MODULATION OF PROTEIN EXPRESSION USING CARBOCYCLIC ARYL ALKENOIC ACID DERIVATIVES

(75) Inventors: Pamela L. Zeitlin, Baltimore, MD (US); Saul Brusilow, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/523,776

(22) Filed: Mar. 11, 2000

(51) Int. Cl.
*A61K 31/19* (2006.01)

(52) U.S. Cl. .................................... 514/570; 514/851

(58) Field of Classification Search ............... 514/570, 514/851
See application file for complete search history.

(56) References Cited

U.S. PATENT DOCUMENTS

| | | | | |
|---|---|---|---|---|
| 4,764,521 A | * | 8/1988 | Herron | 514/381 |
| 5,939,455 A | * | 8/1999 | Rephaeli | 514/547 |
| 5,976,499 A | | 11/1999 | Rubenstein et al. | |
| 5,981,592 A | * | 11/1999 | Wechter et al. | 514/570 |
| 6,048,896 A | | 4/2000 | Giordani et al. | |

FOREIGN PATENT DOCUMENTS

WO   WO 99/40883   *   8/1999

OTHER PUBLICATIONS

Cheng, S. H., et al. "Functional Activation Of The Cystic Fibrosis Trafficking Mutant Delta F508-CFTR By Overexpression", *Am. J. Physiol.* 268, pp. L615-L624, 1995.

Dover, G. J., et al. "Induction Of Fetal Hemoglobin Production In Subjects With Sickle Cell Anemia By Oral Sodium Phenylbutyrate" *Blood* vol. 84, No. 1, pp. 339-343, 1994.

Dover, G. J., et al. "Increased Fetal Hemoglobin In Patients Receiving Sodium 4-Phenylbutyrate [letter]", *N. Engl. J. Med.* vol. 327, No. 8, pp. 569-570, 1992.

Collins, A. F., et al. "Oral Sodium Phenylbutyrate Therapy In Homozygous Beta Thalassemia: A Clinical Trial" *Blood* vol. 85, No. 1, pp. 43-49, 1995.

Batshaw, M.L., et al. "Evidence Of Lack Of Toxicity Of Sodium Phenylacetate And Sodium Benzoate In Treating Urea Cycle Enzymopathies" *J. Inherit. Metab. Dis.* 4:, pp. 231-231, 1981.

Stamatoyannopoulos, G., et al. "Fetal Hemoglobin Induction By Acetate, A Product Of Butyrate Catabolism [see comments]" *Blood* 84:, 3198-3204, 1994.

Candido, E.P., et al. "Sodium Butyrate Inhibits Histone Deacetylation In Cultured Cells" *Cell* 14:, pp. 105-113, 1978.

Rubenstein, R.C., et al. "In Vitro Pharmacologic Restoration Of CFTR-Mediated Chloride Transport With Sodium 4-Phenylbutyrate In Cystic Fibrosis Epithelial Cells Containing Delta F508-CFTR" *J. Clin. Invest.* 100:, pp. 2457-2465, 1997.

(Continued)

*Primary Examiner*—Shengjun Wang
(74) *Attorney, Agent, or Firm*—Edwards Angell Palmer & Dodge LLP; Peter F. Corless; Jeffrey D. Hsi

(57) ABSTRACT

The present invention generally relates to diseases or conditions modulated by undesired protein expression. In one aspect, the methods provide for administration to a mammal, particularly a human, of a therapeutically effective amount of a carbocyclic aryl compound capable of modulating that undesired protein expression. Assays for detecting compounds having desired therapeutic capacity are also provided.

3 Claims, 14 Drawing Sheets

OTHER PUBLICATIONS

Rubenstein, R.C., et al. "A Pilot Clinical Trial Of Sodium 4-Phenylbutyrate (Buphenyl) In Delta F508-Homozygous Cystic Fibrosis Patients: Partial Restoration Of Nasal Epithelial CFTR Function" *Am. J. Resp. Crit. Care Med.* 157:, pp. 484-490, 1998.

Rubenstein, R.C., et al. "Use Of Protein Repair Therapy In The Treatment Of Cystic Fibrosis" *Curr. Opin. Peds.* 10:, pp. 250-255, 1998.

Cheng, S.H., et al. "Detective Intracellular Transport And Processing Of CFTR Is The Molecular Basis Of Most Cystic Fibrosis" *Cell* 63:, pp. 827-834, 1990.

Gething, M.J., et al. "Protein Folding In The Cell" *Nature* 355:, pp. 33-45, 1992.

Hamosh, A., et al. "Cutting CFTR Nonsense Mutations G542X And W1282X Associated With Severe Reduction Of CFTR mRNA In Nasal Epithelial Cells" *Hum. Mol. Genet.* 1:, pp. 542-544, 1992.

Hyde, S.C., et al. "The Effects Of 4-Phenylbutyric Acid On CFTR mRNA Levels" (Abstract), *Pediatr. Pulmonol. Suppl.* 17: pp. 211-212, 1998.

Jiang, C., et al. "Partial Restoration Of cAMP-Stimulated CFTR Chloride Channel Activity In $\Delta$ F508 Cells By Deoxyspergualin" *Am. J. Physiol. Cell Physiol.* 275:, pp. C171-C178, 1998.

McGrath, S.A., et al. "Cystic Fibrosis Gene And Protein Expression During Fetal Lung Development" *Am. J. Respir. Cell Mol. Biol.* 8:, pp. 201-208, 1993.

Ward, C.L., et al. "Degradation Of CFTR By The Ubiquitin-Proteasome Pathway" *Cell* 83:, pp. 121-127, 1995.

Yang, Y., et al. "The Common Variant Of Cystic Fibrosis Transmembrane Conductance Regulator Is Recognized By hsp 70 And Degraded In A Pre-Golgi Nonlysosomal Compartment" *Proc. Natl. Acad. Sci. USA* 90:, pp. 9480-9484, 1993.

Rubenstein, R.C., et al. "Sodium 4-Phenylbutyrate Downregulates Hsc 70: Implications For Intracellular Trafficking Of Delta F508-CFTR" *Am. J. Physiol. Cell Physiol.* 278:, pp. C259-C267, 2000.

Int'l Search Report dated Jul. 24, 2000 re corresponding Int'l Application No. PCT/US00/06377 (one page).

* cited by examiner

Calnexin

Hsp90

Hsp70

Hsp40

Hdj2

US 7,557,144 B1

MODULATION OF PROTEIN EXPRESSION USING CARBOCYCLIC ARYL ALKENOIC ACID DERIVATIVES

STATEMENT OF U.S. GOVERNMENT INTEREST

Funding for the present invention was provided in part by the Government of the United States by virtue of Grant No. PO1-HL-51611 from the National Heart, Lung and Blood Institute. Accordingly, the Government of the United Sates has certain rights to and in the invention claimed herein.

CROSS-REFERENCE TO RELATED APPLICATION

The present application is a continuation-in-part of U.S. Provisional Application No. 60/124,297 filed on Mar. 12, 1999; the disclosure of which is incorporated herein by reference.

FIELD OF THE INVENTION

The present invention features compounds and methods for modulating protein expression and, more particularly, to the use of one or more of such compounds to treat a subject suffering from or susceptible to a condition facilitated by undesired protein expression. Particular compounds of interest include carbocyclic aryl alkenoic acid derivatives. In other aspect, the invention relates to methods for detecting and analyzing such derivatives for therapeutic capacity to treat such conditions.

BACKGROUND

There is almost universal recognition that proteins help define biological systems particularly by influencing cell shape, structure and function. Proteins are generally made by steps that include transcription, translation, trafficking, and for some proteins, secretion or membrane targeting. The ability of the proteins to exist is impacted by degradative processes. See generally, Alberts, Be. et al. (1989) in *Molecular Biology of the Cell* (2nd ed.) Garland Publishing, Inc. New York and London; and Stryer, L. (1988) in *Biochemistry* W.H. Freeman and Co. New York.

Accordingly, nearly all biological systems have evolved several steps (pathways) that collectectively make proteins and then degrade them as needed. The combination of these steps, when focussed on a particular protein or group of proteins, is thought to govern the expression of that protein.

There have been many efforts to modulate protein expression particularly with respect to proteins known or suspected of being involved in mammalian disorders.

For example, one approach has been to identify compounds that can modulate the expression of a particular protein. Following this strategy, a compound can be administered to a primate and especially a human subject to alter at least one synthetic or degradative step to treat a medical condition. This strategy has been used to implement many successful therapies. See generally *The Pharmacological Basis of Therapeutics* (8th ed.) Gilman, A. et al. (eds.) McGraw-Hill Professionals Division, pp. 1264-1276, (1993).

For certain medical conditions, there have been reports that compounds with capacity to modulate protein expression can be used to treat the conditions even if those proteins are damaged.

There have been efforts to treat cystic fibrosis (CF) along these lines.

Briefly, there is understanding that mutations in the cystic fibrosis transmembrane regulator (CFTR) protein can lead to life-threatening illness. One CFTR mutation termed "ΔF508" is a common CFTR mutation. When functioning normally, CFTR is thought to be a necessary cAMP-activated chloride channel. In CF, this channel is thought to be misprocessed and retained in the endoplasmic reticulum of epithelial cells. See e.g., Lukacs et al., *Gastroenterology,* 109:282-284 (1995); Li et al., *Nat. Genet.,* 3:311-316 (1993); and Cheng et al., *Am. J. Physiol,* 268:L615-L624 (1995).

There have been reports that growth of certain cells carrying the CF defect can grow better at reduced temperature or with compounds that alleviate trafficking defects in vitro. See e.g., Egan et al., *Am. J. Physiol.* 271:635-638 (1996); Brown et al., *J. Clin. Invest.,* 99:1432-1444 (1997) and Sato et al., *J. Biol. Chem.,* 271:635-638 (1996).

More generally, steps associated with protein trafficking and especially protein degradation have been disclosed. Some of these steps appear to implement various heat shock protein and/or ubiquitin-associated pathways. See e.g., Gething et al., *Nature,* 355:33-45 (1992) and Chiang et al., *Science,* 246:382-385 (1989)

It has been reported that 4-phenylbutyric acid (sometimes referred to as 4-PBA or Buphenyl), can be used to treat various medical conditions including CF. This compound has been approved for the treatment of certain urea cycle disorders. There has been some discussion that this compound may also find use in the treatment of certain hemoglobinopathies, including sickle cell disease, thalassemias; as well as cancer.

With respect to CF, there have been reports that 4-BPA can restore CFTR-mediated chloride transport. Clinical trials using this compound have provided encouraging results. See Rubenstein, R. C. et al. (1997) *J. Clin. Invest.* 100: 2457-2465; Rubenstein, R. C. (1998) *Am. J. Respir. Crit. Care Med.* 157: 484-490.

Other strategies have been implemented to modulate protein expression. One approach has been to identify compounds that alter the transcription of nucleic acids encoding a protein of interest.

For example, it has been disclosed that 4-PBA can enhance fetal hemoglobin levels by transcriptional "up" regulation. The effective has been reported to involve histone deacetylase. See e.g., Stamatoyannopoulos et al., *Blood,* 84:3198-3204 (1994); Lea et al., *Anticancer Res.,* 15:879-883 (1995).

Accordingly, it would be desirable to have additional compounds and methods for modulating protein expression. It would be especially desirable to have carbocyclic aryl alkenoic acid derivatives and methods for using same that can be used to treat or prevent conditions or diseases impacted by undesired protein expression.

SUMMARY OF THE INVENTION

We have now discovered compounds and therapies to treat or prevent various conditions or diseases modulated by undesired protein expression. More particularly, we have identified therapies that can increase or decrease the expression of particularly proteins, as needed, to treat or prevent such conditions or diseases.

In one aspect, the invention provides important carbocyclic aryl alkenoic acid derivatives that are sometimes referred to herein as "gene" or "protein" drugs. This designation is meant to emphasize that the derivatives represent a new class of compounds that can modulate protein expression at one or more levels. More particular compounds of the invention desirably modulate at least one of transcription, translation, or trafficking of a subject protein or group of such proteins. By the word "trafficking" is meant at least one cell pathway that has been reported to help manipulate protein (or proteins), generally in folded form, to achieve a biological objective. Examples include post-translational modification, protein degradation, secretion, and/or membrane targeting.

Examples of disorders treatable or preventable by the present compounds include those impacted or suspected of being impacted by incorrect (aberrant) protein folding. Such inappropriate folding (misfolding) can encompass all or part of the subject protein. More specific examples of such disorders include those afflicting or thought to inflect one or more of the nervous, hepatic, or respiratory systems.

Additional examples of such disorders include, but are not limited to, lung diseases e.g., those associated with misfolding of surfactant proteins; lung diseases impacted by improper expression of transmembrane proteins including the cystic fibrosis transmembrane regulator (CFTR); liver diseases associated with improper protein trafficking; and brain diseases such as those associated with tangle bodies, e.g., neurofibrillary tangles. More specific brain disorders of interest include those manifested by genetic, infectious (e.g., a viral, bacterial or prion agent) or environmental factors. Other illustrations of such disorders or conditions are provided below.

Therapies of the invention are particularly effective for the treatment and/or prevention of undesired protein expression including those embodiments in which modulated protein expression is desired. By the term "modulate" or related phrase as it is used to reference protein expression is meant an increase or decrease in that expression relative to control (or baseline) expression. Preferred therapies treat, prevent, delay the onset of, or reduce the severity of a targeted mammalian disease or condition.

Particular compounds of the present invention are derivatives of carbocyclic aryl alkenoic acid. Such compounds provide a number of important advantages with respect to prior drugs, particularly derivatives of carbocyclic aryl butyric acid and especially phenyl derivatives of butyric acid, specifically 4-PBA.

For example, we have discovered that certain carbocyclic aryl alkenoic acid derivatives are much more effective especially at low doses (i.e. less than about 10 μM). This advantage can positively impact patient care by providing for lower dose administration while still providing good therapeutic effect. Practice of the invention can thus help to improve patient tolerance while minimizing overall treatment costs. In contrast, the higher dosages often associated with prior drugs may increase chances for patient intolerance and side effects. Importantly, costs associated with the higher dosages may be prohibitive in settings where repeated or prolonged administration is indicated.

In particularly, recognized therapies using 4-PBA often require daily administration of many large tablets, sometimes as much as about 20 to 80 tablets. Such therapies have contributed to substantial patient discomfort and side effects e.g., nausea, muscle cramps and confusion. In contrast, preferred practice of this invention can provide for lower daily dosages, thereby helping to reduce patient discomfort and side effects while still giving good therapeutic effect.

Moreover, we believe that many of the carbocyclic aryl alkenoic acid derivatives of this invention will exhibit greater stability than prior drugs in vitro and in vivo. Without wishing to be bound to any theory, it is believed that the unsaturation of the present derivatives i.e., a double bond in the carbon backbone, can significantly reduce potential for biological transformation into inactive or less active metabolites. In contrast, the prior drugs do not usually have this unsaturation, thereby increasing changes for undesired metabolic conversion of those drugs especially in vivo. This benefit of the invention is very significant as it can improve bioavailability and especially provide for enhanced serum levels of the present derivatives. Importantly, this feature can help reduce the need for repetitive or prolonged administration of the present compounds in many therapeutic settings.

Further, it believed that the unsaturation associated with the present compounds can often assist solubility especially with those aqueous or semi-aqueous solvents typical of many pharmaceutical formulations. In contrast, many of the prior drugs do not have this unsaturation which may, with some solvents, help make those drugs more difficult to use or administer properly.

The therapeutic methods of the invention generally include administering to a subject, particularly a mammal such as a primate and especially a human, a therapeutically effective amount of a compound that can modulate protein expression. More particular compounds that suitably increase or decrease at least one of transcription or trafficking of the subject protein or group of proteins including degradation thereof with respect to control or baseline expression of that protein.

Preferably, an administered compound modulates the expression of a subject protein by at least about 10%, preferably at least about 25%, in at least one of the standard in vitro assays disclosed herein. Exemplary assays detect and preferably measure the protein or nucleic acid encoding same with respect to a suitable control.

In embodiments in which particular carbocyclic aryl alkenoic acid derivatives of this invention are selected for capacity to modulate protein trafficking and especially to inhibit protein degradation, it is preferred that the administered compound exhibit an $IC_{50}$ of at least about 0.001 to about 10 mM in a standard in vitro assay for measuring heat shock protein 70 (hsc70).

For example, in a preferred embodiment of such an hsc70 assay, more preferred compounds features an $IC_{50}$ of about 50 μM or less, still more preferably an $IC_{50}$ of about 1 to about 10 μM or less in the standard in vitro hsp70 assay. Such compounds that inhibit hsc70 protein expression, as determined by the assay, will sometimes be referred to herein as "trafficking inhibitor compounds" or other similar term.

In one embodiment of the foregoing hsp70 assay, the carbocyclic aryl alkenoic acid derivatives can be selected for capacity to boost CFTR protein expression. In this example, preferred compounds increase CFTR expression by at least about 10%, preferably at least about 25%, when compared to control or baseline expression of that protein. Preferably, the compounds will increase CFTR expression by about 50%, and more preferably about 70% to about 100% or more as determined by the assay. In this embodiment, which is sometimes preferred to as a standard in vitro CFTR assay, the assay detects and preferably quantifies presence of degradative complexes that usually include the hsc70 protein. Without wishing to be bound to theory, selected compounds generally assist trafficking by helping CFTR avoid the complexes, thereby reducing or even eliminating significant CFTR degradation. Thus, CFTR expression is assisted in this assay by the trafficking inhibitor compounds. As will be explained in more detail below, such compounds are particularly useful for treating a variety of disorders and conditions including, but not limited to, lung disorders such as CF.

In other invention embodiments in which the carbocyclic aryl alkenoic acid derivatives are selected for capacity to boost protein expression, particularly by increasing transcription of a subject protein (or group thereof), it is generally preferred that the administered compound exhibit at least about a 10%, preferably at least about a 25% increase in transcription when compared to a suitable control or baseline experiment. Preferably, the increase in transcription provided by the compounds will be between from about 20% to about 50%, more preferably between from about 60% to 70% as measured in a standard in vitro assay for transcription. An example includes a conventional nuclease protection assay. Such compounds are sometimes referred to herein as "transcription enhancing" compounds or like term. In many instances, expression of the subject protein(s) will be increased by such transcription enhancing compounds.

Compounds useful in the invention include carbocyclic aryl compounds substituted with a carboxy acid (—COOH); protected carboxy acid such as an ester, particularly an alkyl ester such as e.g. —COOR where R is alkyl, preferably $C_{1-8}$ alkyl; sulfonic acid (—$SO_3H$); nitro; cyano; haloalkyl particularly perhaloalkyl such as trifluoromethyl and pentafluoroethyl, where such a polar functional group is spaced from the carbocyclic aryl ring, e.g. by a linker group containing 1 to about 16 carbons, more typically 1 to about 8 or 12 carbons, still more typically a linker of about 1, 2, 3, 4, 5, or 6 carbons. The polar functional group (i.e. carboxy acid, ester, sulfonic acid, nitro, cyano, haloalkyl) is preferably on the terminal carbon of the linker. The linker may contain one or more unsaturated carbons, preferably a carbon-carbon double bond, although alkynylene linkages also may be present. If a carboxy group is present, the linker group preferably contains a carbon-carbon multiple bond, particularly an alkenylene linkage. The linker also may contain a hetero atom (N, O or S) in the linker chain. Typical carbocyclic aryl groups substituted with a polar functional group include e.g. phenyl, naphthyl, acenaphtyl, anthracenyl, and the like, with phenyl being preferred. The carbocyclic aryl group also may have ring substituents such as halo (particularly F, Cl, and Br); alkyl particularly $C_{1-8}$ alkyl), cyano, nitro.

More preferred compounds of this invention are provided in the discussion and Examples that follow.

Suitable compounds of this invention can be readily identified or confirmed by simple testing, e.g., by in vitro testing of a candidate compound relative to a control for the ability to modulate protein expression, e.g. by at least 10% relative to the control. In some invention embodiments, it may be useful to include, as a separate working control, an assay that includes 4-phenyl butyric acid (4-PBA) as the control. In this embodiment, preferred compounds of the invention will show better activity than 4-PBA especially at low dosages. That is, such compounds will show at least about a 10 fold increase in activity with respect to the same amount of 4-PBA in the assay, preferably about a 50 to 100 fold increase and more preferably about a 100 to about a 1000 fold increase in activity.

The invention further relates to methods of detecting and analyzing compounds that modulate protein expression and exhibit therapeutic capacity to treat or prevent the above-described conditions. Preferred detection and analysis methods include both in vitro and in vivo assays to determine the therapeutic capacity of agents to modulate the expression of one or a group of subject proteins.

Preferred in vitro detection assays according to the present invention detect and usually quantify modulated protein expression by analyzing specific steps or pathways known or through to impact expression.

For example, in one embodiment, such an assay will include the following steps 1) through 4):

1) culturing a population of cells capable of expressing at least one heat shock protein, preferably hsc70,
2) adding at least one known or candidate compound to the cells, preferably the carbocyclic aryl alkenoic acid derivatives;
3) measuring at least one step capable of increasing or decreasing the protein expression; and
4) determining the effect of the known or candidate compound on the expression of subject protein(s).

In the foregoing general assay, particular steps of interest include transcription, translation, and protein trafficking including, but not limited to, steps or pathways associated with particular molecular complexes such as those impacting protein degradation. A preferred candidate compound is a carbocyclic aryl alkenoic acid derivative. As discussed, the method can be adapted to detect and preferably quantify hsc70 expression, CFTR expression, or both. In this examples of the invention, the hsc70 and/or the CFTR can be provided to the cells as a heterologous or homologous proteins as needed. In embodiments in which heterologous expression is desired, the protein may be suitably provided by standard recombinant strategies involving expression or co-expression of vectors that encode the protein.

The foregoing general assay can effectively measure the capacity of a desired compound to modulate protein expression by detecting and preferably quantifying increases or decreases in transcription or protein trafficking. References herein to a "standard in vitro assay" or other similar phase refers to the above protocol of steps 1) through 4).

In particular, when step 3) of the standard in vitro assay is implemented to measure hsc70 protein expression, the assay will be more specifically referred to as the standard in vitro hsc70 assay. When the assay is adapted to measure CFTR expression, the assay will be referred as an in vitro CFTR assay. In the latter assay, the CFTR expression is suitably measured according to standard methods such as those discussed below. Preferred assays of this type involve immunological detection strategies such as immunoprecipitation or related approaches.

Alternatively, in embodiments when step 3) of the standard in vitro assay measures transcription of a subject protein (or group or proteins), the assay will often be referenced as a standard in vitro assay for measuring transcription of nucleic acid encoding the protein or similar term. As described below and in the Examples following, a preferred in vitro transcription assay is a nuclease protection assay.

As will be apparent, the in vitro assays of the present invention can be conducted with nearly any population of cells that can express at least one heat shock protein and particularly hsc70 including a lysate of such cells or tissue, or a substantially purified fraction of the lysate. Suitably expressing cells that may be employed in the assay include, but are not limited to, primary cells such as nasal epithelia, and certain immortalized cells having demonstrated capacity to express, as a heterologous to homologous protein, mammalian and especially human proteins e.g., hsc70 and CFTR. Preferred examples of such cells are provided below.

The in vitro detection assays of the invention can be adapted in accordance with intended use. For example, as noted above, it has been found that protein expression is substantially impacted by transcription and trafficking of the subject protein(s). As discussed, the standard in vitro assay generally outlined above can be modified, e.g., at step 3) above to include measurements of desired steps such as transcription or protein trafficking including measurement of hsp70 expression as degradative complexes. The known or candidate compound can be employed in the assays as a sole active agent or in combination with other agents including other recognized modulators of protein expression, e.g., transcriptional inhibitors, protein trafficking inhibitors and the like. Examples of such agents include, but are not limited to, 4-PBA and hydroxyurea.

In most instances, the in vitro assays are performed with a suitable control assay usually including or consisting of the same test conditions as in the steps above, but without adding the compound or compounds to be tested. In such cases, a candidate compound can be identified as exhibiting desired activity by exhibiting at least about 10% change in the specified activity relative to the control; more preferably at least about 20% change relative to the control assay; and still more preferably at least about a 30% to about a 100%, change relative to the control. By the word "change" is meant an increase or decrease relative to that control.

The invention is compatible with recognized in vivo assays to determine the therapeutic capacity of a known or candidate compound to modulate protein expression and particularly to treat a disease or conditions impacted by such expression. The monitored disease or condition suitably may be pre-exist in the test animal, or the cell function may be induced, e.g., genetically, chemically, or by surgical intervention. Animal functions that can be suitably assayed in these methods include, but are not limited to, transcription, translation, post-translational modification, trafficking including the degradation of subject proteins, cell proliferation including metastases, cell division, apoptosis, respiratory function, cognition, membrane potential, intracellular or extracellular ion concentration, intracellular kinase activity, phosphatase activity, intracellular protein transport, endogenous or heterologous gene expression, chloride channel function and protein secretion.

Suitable in vivo assays can be modified in a number of ways as needed. For example, in certain embodiments of the present invention, a specific carbocyclic aryl alkenoic acid derivative is administered to the animal either as a sole active agent or in combination with other active compounds (e.g., 4-PGA), including other compounds of this invention to be tested. In most embodiments, activity of the compound in a given in vivo assay is compared to a suitable control (e.g., a control animal not receiving the compound). Typically, the control assay is conducted the same as the test assay but without administering the compound to the test subject. A variety of test subjects can be employed, particularly mammals such as rabbits, primates, various rodents and the like including mice. Preferred test subjects are recognized models for a particular human disease or disorder.

If desired, the in vitro efficacy of a particularly carbocyclic aryl alkenoic acid derivative can be tested in recognized human CF model i.e., nasal potential differences between normal and CF patients. Generally, the derivative is administered to the human subject in a therapeutically effective amount for several days. Nasal tissue is removed and chloride transport detected and preferably measured in control (normal patient) and CF patients. Additionally preferred compounds of this invention will help restore normal CFTR function in the nasal epithelial cell surface to level that is comparable to that achieved with 4-PBA. A preferred assay of this type is provided below in Example 13.

As noted above, the detection assays (either in vitro or in vivo) can be conducted in a wide variety of cells. If desired, the assays can also be conducted with tissues and organs that include such cells. Further, the assays can detect useful compounds by measuring the activity of target molecules such as nucleic acids and proteins in pathways that modulate protein expression. Thus, the present assays are readily adapted to measure activity in a variety of cell, tissue and organ settings.

Significantly, use of multiple detection assays (e.g., a combination of the in vitro and/or in vivo assays) with a single compound such as a particular carbocyclic aryl alkenoic acid derivative as provided herein can extend the selectivity and sensitivity of detection as desired.

Such broad spectrum testing provides advantages. Thus, for example, in vitro assays of the invention can efficiently perform multiple analysis, thereby enhancing efficiency and probability of identifying compounds with therapeutic capacity. This is especially useful when large numbers of compounds need to be tested. For instance, libraries of candidate compounds and particularly libraries or carbocyclic aryl alkenoic acid derivatives can be made by standard synthetic methods including combinatorial-type chemistry manipulations and then tested in accord with the invention.

Additionally provided by the invention are useful kits for performing the methods of those invention. Preferred kits include at least one container means that includes at least one of the carbocyclic aryl compounds disclosed herein.

Other aspects of the invention are discussed below.

DETAILED DESCRIPTION OF THE INVENTION

Figure 1A:
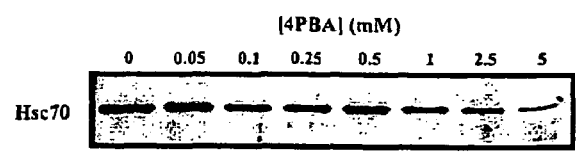
FIG. 1A is a representation of a Western Blot showing hsc70 expression as a function of added 4-PBA in IB3-1 cells.

As discussed above, the present invention features therapeutic methods for treatment and prevention of conditions modulated by unacceptable protein expression. the treatment methods of the invention generally include administering a therapeutically effective amount of at least one carbocyclic aryl alkenoic acid derivative to a subject, preferably a mammal such as a primate and often a human patient in need of such treatment.

The therapeutic methods of the invention generally comprise administration of a therapeutically effective amount of at least one and preferably one compound to the subject. Treatment methods of the invention also comprise administration of an effective amount of a compound of Formula I as defined herein to the subject, particularly a mammal such as a human in need of such treatment for an indication disclosed herein.

Typical mammalian subjects are human patients suffering from, recovering from, or susceptible to those conditions discussed above, e.g., lung diseases afflicting normal alveolar function and including those associated with misfolding of surfactant protein protein C; lung diseases impact by improper expression of the cystic fibrosis transmembrane regulator (CFTR) including CF; liver diseases including α1 anti-trypsin disease; and brain diseases such as Alzheimer's disease and related dementia.

Other specific diseases of interest include Marfan syndrome, familial hypercholesterolemia and Tay-Sachs disease; as well as related disorders. See Bradbury, N. A. (2000) in *Am. J. Physiol. Cell Physiol.* 278: C257-C258 and references cited therein. See also Zeitlan, P. L. (2000) in *Molecular Therapy* 1: 1 for a information relating to current CF therapeutic approaches.

A variety of compounds in accord with this invention can be employed in the present treatment methods. Simple testing, e.g., in a standard in vitro assay as defined above, can readily identify suitable compounds. Particularly preferred compounds for use in accordance with the invention are of the following Formula I:

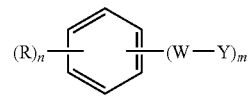

I wherein each W is the same or different linker group such as optionally substituted alkylene preferably having 1 to about 12 chain carbons, more preferably 1 to about 8 chain carbons, still more preferably 1, 2, 3 or 4 chain carbons; optionally substituted alkenylene preferably having 2 to about 12 chain carbons, more preferably 2 to about 8 chain carbons, still more preferably 2, 3 or 4 alkenylene chain carbons; optionally substituted alkynylene preferably having 1 to about 12 chain carbons, more preferably 2 to about 8 chain carbons, still more preferably 2, 3 or 4 alkynylene chain carbons; optionally substituted heteroalkylene preferably having 1 to about 12 chain carbons, more preferably 1 to about 8 chain carbons, still more preferably 1, 2, 3 or 4 heteroalkylene chain carbons; optionally substituted heteroalkenylene preferably having 2 to about 12 chains carbons, more preferably 2 to about 8 chains carbons, still more preferably 1, 2, 3, 4 heteroalkylene chain carbons; or optionally substituted heteroalkynynylene preferably having 2 to about 12 chain carbons, more preferably 2 to about 8 chain carbons, still more preferably 2, 3 or 4 heteroalkylene chain carbons;

each Y is independently a carboxy acid, a protected carboxy acid, sulfonic acid, nitro, cyano or haloalkyl;

R is a non-hydrogen substituent such as halogen, cyano, nitro, optionally substituted alkyl preferably having 1 to about 20 carbons, more preferably 1 to about 12 carbons; optionally substituted alkenyl preferably having 2 to about 20 carbon atoms, more preferably 2 to about 12 carbon atoms; optionally substituted alkynyl preferably having 2 to about 20 carbon atoms, more preferably 2 to about 12 carbon atoms; optionally substituted alkoxy preferably having from 1 to about 20 carbon atoms, more preferably 1 to about 12 carbon atoms; optionally substituted alkylthio preferably having from 1 to about 20 carbon atoms, more preferably 1 to about 12 carbon atoms; optionally substituted alkylsulfinyl preferably having from 1 to about 20 carbon atoms, more preferably 1 to about 12 carbon atoms; optionally substituted alkylsulfonyl preferably having from 1 to about 20 carbon atoms, more preferably 1 to about 12 carbon atoms; optionally substituted carbocyclic aryl having at least about 6 ring carbon atoms; optionally substituted aralkyl having at least about 6 ring carbon atoms;

m is an integer of from 1 to 6, and preferably m is 1 or 2, more preferably m is 1; n is an integer of from 0 (where no R groups are present) to 5, and preferably n is 0, 1 or 2; and pharmaceutically acceptable salts thereof, with the exclusion of 4-phenylbutyric acid.

Preferred compounds of Formula I have an unsaturated linker group, such as those of following Formula IA:

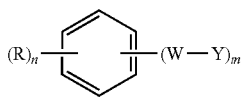

wherein each W is the same or different optionally substituted alkenylene preferably having 2 to about 12 chain carbons, more preferably 2 to about 8 chain carbons, still more preferably 2, 3 or 4 alkenylene chain carbons; optionally substituted alkylnylene preferably having 1 to about 12 chain carbons, more preferably 2 to about 8 chain carbons, still more preferably 2, 3 or 4 alkylene chain carbons; optionally substituted heteroalkylenylene preferably having 2 to about 12 chain carbons, more preferably 2 to about 8 chain carbons, still more preferably 1, 2, 3, 4 heteroalkylene chain carbons; or optionally substituted heteroalkynynylene preferably having 2 to about 12 chain carbons, more preferably 2 to about 8 chain carbons, still more preferably 2, 3 or 4 heteroalkynylene chain carbons;

Y, R, m and n are the same as defined in Formula I; and pharmaceutically acceptable salts thereof.

Particularly preferred compounds of Formula I have an alkenylene linker group, such as those of following Formula IB:

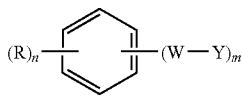

wherein each W is the same or different optionally substituted alkenylene preferably having 2 to about 10 chains carbons, more preferably 2 to about 8 chain carbons, still more preferably 2, 3, 4 or 5 alkenylene chain carbons;

Y, R, m and n are the same as defined in Formula I; and pharmaceutically acceptable salts thereof.

Specifically preferred compounds for use in methods of the invention include sterioisomers of the foregoing compounds according to Formulae I, IA and IB above. More are cis and trans isomers of 4-phenyl-Δ3-butenoic acid and 4-phenyl-Δ2-butenoic acid. More specifically preferred are the following trans isomers of those compounds shown below in Table I.

TABLE I 4-phenyl-Δ3-transbutenoic acid

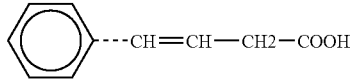

4-phenyl-Δ2-transbutenoic acid

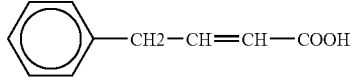

Suitable alkyl substituent groups of compounds of the invention (which includes compounds of Formulae I, IA, IB as defined above) typically have from 1 to about 12 carbon atoms, more preferably 1 to about 8 carbon atoms, still more preferably 1, 2, 3, 4, 5, or 6 carbon atoms. As used herein, the term alkyl unless otherwise modified refers to both cyclic and noncyclic groups, although of course cyclic groups will comprise at least three carbon ring members. Preferred alkenyl and alkynyl groups of compounds of the invention have one or more unsaturated linkages and typically from 2 to about 12 carbon atoms, more preferably 2 to about 8 carbon atoms, still more preferably 2, 3, 4, 5, or 6 carbon atoms.

The terms alkenyl and alkynyl as used herein refer to both cyclic and noncyclic groups, although straight or branched noncyclic groups are generally more preferred. Preferred alkoxy groups of compounds of the invention include groups having one or more oxygen linkages and from 1 to about 12 carbon atoms, more preferably from 1 to about 8 carbon atoms, and still more preferably 1, 2, 3, 4, 5 or 6 carbon atoms. Preferred alkylthio groups of compounds of the invention include those groups having one or more thioether linkages and from 1 to about 12 carbon atoms, more preferably from 1 to about 8 carbon atoms, and still more preferably 1, 2, 3, 4, 5, or 6 carbon atoms. Preferred alkylsulfinyl groups of compounds of the invention include those groups having one or more sulfoxide (SO) groups and from 1 to about 12 carbon atoms, more preferably from 1 to about 8 carbon atoms, and still more preferably 1, 2, 3, 4, 5, or 6 carbon atoms. Preferably alkylsulfonyl groups of compounds of the invention include those groups having one or more sulfonyl ($SO_2$) groups and from 1 to about 12 carbon atoms, more preferably from 1 to about 8 carbon atoms, and still more preferably 1, 2, 3, 4, 5 or 6 carbon atoms. Preferred aminoalkyl groups include those groups having one or more primary, secondary and/or tertiary amine groups, and from 1 to about 12 carbon atoms, more preferably 1 to about 8 carbon atoms, still more preferably 1, 2, 3, 4, 5, or 6 carbon atoms. Secondary and tertiary amine groups are generally more preferred than primary amine moieties. Suitable heteroaromatic groups of compounds of the invention contain one or more N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazole. Suitable heteroalicyclic groups of compounds of the invention contain one or more N, O or S atoms and include, e.g., tetrahydrofuranyl, thienyl, tetrahydropyranyl, piperidinyl, morpholino and pyrrolindinyl groups. Suitable carbocyclic aryl groups of compounds of the invention include single and multiple ring compounds, including multiple ring compounds that contain separate and/or fused aryl groups. Typical carbocyclic aryl groups of compounds of the invention contain 1 to 3 separate or fused rings and from 6 to about 18 carbon ring atoms. Specifically preferred carbocyclic aryl groups include phenyl; naphthyl including 1-naphthyl and 2-naphthyl; biphenyl; phenanthryl; anthracyl; and acenaphthyl. Substituted carbocyclic groups are particularly suitable including substituted phenyl, such as 2-substituted phenyl, 3-substituted phenyl, 4-substituted phenyl, 2,3-substituted phenyl, 2,4-substituted phenyl, and 2,4-substituted phenyl; and substituted naphthyl, including naphthyl substituted at the 5, 6 and/or 7 positions.

Suitable aralkyl groups of compounds of the invention include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and methylenenaphthyl (—$CH_2$-naphthyl), and other carbocyclic aralkyl groups, as discussed above.

As discussed above, the foregoing R, W and Y groups are optionally substituted. A "substituted" R, W and Y group or other substituent may be substituted by other than hydrogen at one or more available positions, typically 1 to 3 or 4 positions, by one or more suitable groups such as those disclosed herein. Suitable groups that may be present on a "substituted" R, W and Y group or other substituent include e.g. halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups having those having one or more oxygen linkages and from 1 to about 12 carbon atoms, or 1, 2, 3, 4, 5 or 6 carbon atoms; aryloxy such as phenoxy; alkylthio groups including those moieties having one or more thioether linkages and from 1 to about 12 carbon atoms, or 1, 2, 3, 4, 5 or 6 carbon atoms; alkylsulfinyl groups including those moieties having one or more sulfinyl linkages and from 1 to about 12 carbon atoms, or 1, 2, 3, 4, 5, or 6 carbon atoms; alkylsulfonyl groups including those moieties having one or more sulfonyl linkages and from 1 to about 12 carbon atoms, or 1, 2, 3, 4, 5, or 6 carbon atoms; aminoalkyl groups such as groups having one or more N atoms and from 1 to about 12 carbon atoms, or 1, 2, 3, 4, 5 or 6 carbon atoms; carbocyclic aryl having 6 or more carbons, particularly phenyl (e.g. an R group being a substituted or unsubstituted biphenyl moiety); aralkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

Compounds in accord with this invention can be obtained from commercial sources or readily prepared by conventional procedures or those requiring a minimum of experimentation. Suitable commercial vendors include the Aldrich Chemical Co. (Milwaukee, Wis.), the Sigma Chemical Co. (St. Louis, Mo.), and Fluka (Milwaukee, Wis.).

Particular methods for making compounds of this invention have been reported. For example, see the Chapman & Hall Chemical database as provided by Dialog® File 303 (Cary, N.C.) citing the following references: Linstead, R P et al. *JCS* (1926) 2741; Gerkin, R. M. et al. *JACS* (1967) 89: 5850; Watt D. S. et al. *JACS* (1977) 99: 182; Wolber E K A et al. *CBER* (1992) 125: 525; and Nakanishi S et al. *SYNTH* (1994) 609; the disclosures of which are incorporated herein by reference. See also McMurry, J. (1992) in *Organic Chemistry* Brooks/Cole Publishing Co. Pacific Groove, Calif.

In the therapeutic methods of the invention, a treatment compound can be administered to a subject by one or a combination of ways. For example, a carbocyclic aryl alkenoic acid derivative can be administered as a prophylactic to prevent the onset of or reduce the severity of a targeted condition. Alternatively, the compound can be administered during the course of or following recovery from a targeted condition.

A treatment compound can be administered to a subject, either alone or in combination with one or more therapeutic, inert or partially active agents, as a pharmaceutical composition in mixture with conventional excipient, i.e. pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers includes but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Such compositions may be prepared for use in parenteral administration, particularly in the form of liquid solutions or suspensions; for oral administration, particularly in the form of tables or capsules; intranasally, particularly in the form of powders, nasal drops, or aerosols; vaginally; topically e.g. in the form of a cream; rectally e.g. as a suppository; etc.

The pharmaceutical agents may be conveniently administered in unit dosage form and may be prepared by any of the methods well known in the pharmaceutical arts, e.g., as described in *Remington's Pharmaceutical Sciences* (Mack Pub. Co., Easton, Pa. 1980). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain compounds or formulations thereof.

Other potentially useful parenteral delivery systems include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration. Other delivery systems will administer the therapuetic agent (s) directly at a targeted site, e.g., by stent, needle or related implementation.

A compound according to this invention can be employed in the present treatment methods as the sole active pharmaceutical agent or can be used in combination with other active ingredients, e.g., 4-PBA, hydroxyurea or other suitable compounds including one or more other carbocyclic aryl compounds. See *Proc. Natl. Acad. Sci.* (2000) 97: 1796-1780 for additional information relating to 4-PBA and particularly to its use a therapuetic agent.

The concentration of one or more treatment compounds in a therapeutic composition will vary depending upon a number of factors, including the dosage of the compound to be administered, the chemical characteristics (e.g., hydrophobicity) of the compositions employed, and the intended mode and route of administration. In general terms, one or more than one of the compounds may be provided in an aqueous physiological buffer solution containing about 0.1 to 10% w/v of a compound for parenteral administration.

In will be appreciated that the actual preferred amounts of active compounds used in a given therapy will vary according to e.g. the specific compound being utilized, the particular composition formulated, the mode of administration and characteristics of the subject, e.g. the species, sex, weight, general health and age of the subject. Optimal administration rates for a given protocol of administration can be readily ascertained by those skilled in the art using conventional dosage determination tests conducted with regard to the foregoing guidelines. Suitable dose ranges may include from about 1 µg/kg to about 100 mg/kg of body weight per day.

Therapeutic compounds of the invention are suitably administered in a protonated and water-soluble form, e.g., as a pharmaceutically acceptable salt, typically an acid addition salt such as an inorganic acid addition salt, e.g., a hydrochloride, sulfate, or phosphate salt, or as an organic acid addition salt such as an acetate, maleate, fumarate, tartrate, or citrate salt. Pharmaceutically acceptable salts of therapeutic compounds of the invention also can include metal salts, particularly alkali metal salts such as a sodium salt or potassium salt; alkaline earth metal salts such as a magnesium or calcium salt; ammonium salts such an ammonium or tetramethyl ammonium salt; or an amino acid addition salts such as a lysine, glycine, or phenylalanine salt.

Preferred compounds of this invention feature significant activity in a standard in vitro hsc70 assay. Typically, the derivatives will inhibit or decrease, preferably decrease hsc70 levels in the assay by at least about 10%, preferably at least about 25% when compared to a suitable control.

In particular embodiment of such an assay, between about 0.1 mM to about 500 mM, preferably 0.5 mM to about 10 mM, of a compound to be tested is used. The foregoing carbocyclic aryl alkenoic compounds will often be preferred. Exemplary assays include monitoring at least one of hsc70 transcription, translation, or protein trafficking including measurement of complexes that include hsc70 and particularly those hsc70 comprises involved n the degradation of proteins such as the CFTR.

A preferred assay monitors hsc70 transcription by the following nuclease protection assay;
  a) culturing cells capable of expressing at least one heat shock protein, preferably hsc70 in suitable medium (e.g., DMEM, LHC-8) and adding a compound to be tested, e.g., an carbocyclic aryl alkenoic acid derivative, to the medium for between from about 6 hours to about 72 hours,
  b) preparing a lysate from the cells and isolating RNA from same preferably under conditions that reduce or eliminate RNA degradation,
  c) hybridizing the RNA in the lysate to a probe capable of specifically binding a nucleic acid sequence encoding the heat shock protein, e.g., hsc70 protein, the hybridization being capable of forming a specific binding pair, usually under high stringency conditions, after about 6 hours to about 24 hours,
  d) contacting the specific binding pair with a nuclease such as RNAse, the nuclease being capable of degrading any single stranded nucleic acid in the lysate; and
  e) detecting the specific binding pair as being indicative of the level of heat shock protein and particularly hsc70 protein transcription in the cells.

Preferred hsc70 probe and RNAse protection experiments are provided in the Examples following. Typically, the amount of hsc70 specific RNA or mRNA detected in the presence of the compound is compared to a suitable control, which control is treated under the same conditions as the assay culture but does not include the compound that is tested. General guidance relating to performing nuclease protection assays can be found in Sambrook et al. in *Molecular Cloning: A Laboratory Manual* (2d ed. 1989); and Ausubel et al. (1989), *Current Protocols in Molecular Biology,* John Wiley & Sons, New York.

Particular reference herein to a "standard hsc70 nuclease protection" assay or related phrase refers to the steps a) through e) above in which nucleic acid encoding the hsc70 protein is tested. Such an assay can be readily modified, if desired, to include monitoring of other RNAs including mRNA encoding proteins such as CFTR and/or control proteins such as those specifically mentioned below. Preferred assays will include a conventional quantative technique such as densitometry in embodiments in which good measurement and data analysis is needed.

Further preferred compounds will exhibit an $ID_{50}$ of about 500 µM or less, still more preferably an $IC_{50}$ of about 1 to about 10 µM or less in the standard in vitro hsp70 nuclease protection assay. Compounds such as the carbocyclic aryl alkenoic acid derivatives disclosed herein exhibiting such preferred activity are considered to be good trafficking inhibitor compounds.

As mentioned, the foregoing nuclease protection assay can be readily adapted to monitor other nucleic acids such as those encoding other proteins besides hsc70. Such as assay may be particularly useful in embodiments in which a compound of this invention is tested for capacity to increase transcription of the nucleic acid. For example, in one approach, the hsp70 probe described above can be substituted with another probe that specifically binds the subject nucleic acid preferably under high stringency conditions.

Other examples of useful probes include those useful for measuring hemoglobin, and surfactant protein expression. See e.g., Peterec, S. M. et al. (1994) *Physiol. Lung Cell. Mol. Physiol.* 267: 12784-12788; and Collins et al. (1995) *Blood* 85; 43-49.

Other suitable probes for use in accord with this invention can be found at the National Center for Biotechnology Information (NCBI)- Genetic Sequence Data Bank (Genbank). A suitable sequence listing can be obtained from Genbank at the National Library of Medicine, 38A, 8N05, Rockville Pike, Bethesda, Md. 20894. Genbank is also available on the internet at http://www.ncbi.nlm.nih.gov. See generally Benson, D. A. et al. (1997) *Nucl. Acids. Res.* 25: 1 for a description of Genbank.

Suitable probe lengths in the assays will generally vary depending on intended use but will generally be from about 50 nucleotides to about 5000 nucleotides in length, preferably about 1000 to about 500 nucleotides.

A particular assay for monitoring hsc70 protein in vitro is by conducting the following immunoprecipitation assay:
  a) culturing cells capable of expression at least oneheat shock protein, preferably hsc70 protein, in medium and adding a compound to be tested, e.g., a carbocyclic aryl alkenoic acid derivative, to the medium for between from about 6 hours to about 72 hours,
  b) preparing a lysate from the cells at reduced temperature in RIPA buffer under conditions that help to minimize protein degradation in the lysates,
  c) contacting the lysate with a first antibody capable of binding hsc70 protein as an immune complex, the contacting being under conditions sufficient to form the immune complex,
  d) separating the immune complex from the lysate preferably by chromatography on a suitable protein A-Sepharose 4B matrix; and
  e) detecting the immune complex as being indicative of the hsc70 in the cells.

Preferred detection formats include Western immunoblots in which second antibodies are used to bind the immune complex. Such second antibodies can be detectably labeled themselves or detectably labeled third antibodies can be used that bind, preferably specifically, the second antibody bound to the immune complex. General guidance relating to performing this assay can be found in Harlow and Lane (eds) in: *Antibodies: A Laboratory Manual* 1988, Cold Spring Harbor Laboratory, New York. Also see Harlow, et al. for examples of strategies for detectably labeling the antibodies. Suitable antibodies can be polyclonal or monoclonal as needed.

A more specific hsc70 immunoprecipitation assay is provided in the discussion and Examples following. Typically, the amount of hsc70 protein detected in the presence of the compound is compared to a suitable control, which control is treated under the same conditions as the assay culture but does not include the compound that is tested.

Particular reference herein to a "standard hsc70 protein" assay or related phrase refers to the steps a) through e) above. Such as assay can be readily modified, if desired, to include monitoring of other proteins such as other heat shock proteins, CFTR and/or control proteins such as those mentioned below. Typically, the assay will include a conventional quantative technique such as densitometry.

In a particular embodiment of the standard in vitro hsc70 protein assay mentioned above, the assay further detects CFTR, especially human CFTR. In this example, the assay is suitably adapted so that CFTR is detected in the lysates. In one approach, step e) is modified so that presence of the CFTR in the immune complexes is detected and preferably quantified. In one embodiment, the lysate is contacted with a first antibody capable of binding CFTR. Binding of the first antibody can be readily detected by binding of a second detachably labeled antibody according to conventional immunological methods. This embodiment of the hsc70 assay will be referred to herein as a "standard in vitro CFTR assay" or related term to denote supplemental or exclusive detection of the CFTR.

More specific guidance relating to performing the standard in vitro CFTR assay can be found in the discussion and Examples following. See also Rubenstein, R. C. and P. L. Zeitlan (2000) *Am. J. Physiol. Cell Physiol.* 278: C259-C267.

As will become more apparent from the following examples, a decrease in the amount of CFTR detected in the standard in vitro CFTR assay is taken to be indicative of an increase in the level of functional or potentially functional CFTR. That is, less CFTR in the immune complex and especially those complexes that include or consist of hsc70 is taken to be indicative of less transmembrane protein available for degradation. Accordingly, CFTR expression levels increase in the assay in line with a decrease in the amount of degradative complexes. See also Rubenstein, R. C., (2000), supra and the Examples below.

Additionally preferred carbocyclic aryl alkenoic acid derivatives are capable of inhibiting specific enzymes such as histone deacetylase. Additionally preferred derivatives serve as good amino acid acylating agents. Methods for detecting inhibition of histone deacytlase are known in the field. See e.g., Candido, E. P. et al. (1978) *Cell* 14: 105-113; and Lea, M A and N. Tulsyan (1995) *Anticancer Res.* 15: 879-883. Methods for detecting amino acid acylation are also known and include use of conventional chromatographic approaches, e.g., HPLC.

See also the U.S. Pat. No. 5,976,499 (U.S. Ser. No. 09/148, 122) for additional methods for screening compounds capable of treating CF; the disclosure of which is incorporated herein by reference.

As noted above, the present invention includes methods of detecting and analyzing compounds such as carbocyclic aryl alkenoic acid derivatives with therapeutic capacity to treat or prevent any of the above-mentioned diseases or disorders. A disease or condition is impacted or modulated by protein expression if afflicted cells, tissue and/or organs exhibit an increase or decrease in subject protein (or proteins) of at least about 2 fold, preferably about 2 to 1000-fold, more preferably about 2- to 100-fold, and more typically about 2- to 10-fold relative to a suitable control. That control is typically the same cells, tissues and/or organs taken from a normal or unafflicted subject. The change in protein expression can be measured by methods referenced herein including those in vitro and in vivo assays in which subject proteins are measured. Without being bound by theory, it appears that preferred carbocyclic aryl alkenoic acid derivatives modulate protein expression particularly by increasing transcription and/or reducing unwanted protein degradation. Accordingly, the compositions and methods of this invention are particularly useful in the treatment of conditions or disorders modulated by such protein expression.

Preferred cells for use in the methods of this invention include those expressing heat shock proteins and particularly hsc70. As mentioned previously, suitable cells can be an immortalized cell line or primary culture of cells (e.g., obtained form a tissue or organ such as the nose). More preferred cells manifest a change in protein expression following contact with a suitable molecule such as 4-PBA, i.e., at least about a 10% increase or decrease relative to a suitable control. More suitable cells include those amenable to standard recombinant DNA techniques such as transformation (e.g., mediated by calcium, biolistic transfer, electroporation and the like) by a vector that encodes the subject protein. Examples include CFTR and especially human CFTR. The human CFTR sequence has been disclosed. For example, see the Genbank website referenced above.

If needed, one or a combination of strategies can identify such cells. For example, in one approach, about $1 \times 10^5$ cells are seeded in petri dishes in suitable growth medium. For primary cultures of cells, a desired tissue or organ is obtained from an animal and dispersed according to standard methods (e.g., by sonication, mechanical agitation, and/or exposure to dispersing agents known in the field, e.g., detergents and proteases). After one or a few days, the growth medium is removed from the petri dish and the cells washed with phosphate-buffered saline. The cells are then contacted with about 0.01 mM to about 5 mM 4-PBA or 4-phenyl-Δ3-butenoic acid in the culture. After exposing the cells to the 4-BPA for about a few hours up to about 24 hours, the medium is removed and the cells lysed in an appropriate lysis buffer such as those described herein. The cells are then assayed according to any of the method described herein for response to the added 4-PBA or 4-phenyl-Δ3-butenoic acid. Examples of such cells include immortalized cystic fibrosis bronchiolar epthelial cells such as those referenced below, e.g., IB3-1 cells. Other examples of such primary cells include nasal epithelia.

A control experiment is generally tailored for use in a particular assay. For example, most control experiments involve subjecting a test sample (e.g., a population of suitable cells or lysate thereof) to medium, saline, buffer or water instead of a compound to be tested in parallel to the cells receiving an amount of test compound. A desired assay is then conducted in accordance with the present methods. Specific examples of suitable control experiments are described below.

Specific techniques for use with the methods described herein may involve one or more standard laboratory manipulations such as chemiluminescence tests, thin layer chromatography (TLC) separations, nucleic acid isolation and purification, SDS-PAGE gel electrophoresis, autoradiography, scintillation counting, densitometery, Northern and Western Blot hybridization, and immunoassays (e.g., RIA and ELISA tests). See generally Sambrook et al. (1989), supra; and Ausubel et al. (1989), supra. Alternatively, or in addition, recognized gas or high performance liquid chromatography (HPLC) may also be used as needed.

As discussed, preferred compounds of this invention are derivatives of carbocyclic aryl alkenoic acid. Exemplary of such derivatives are phenylcarbocyclic aryl alkenoic acid derivatives including 4-phenyl-Δ3-transbutenoic acid. That acid can, under certain conditions, be β oxidized to phenylacetic acid which serves as an amino acid acylating agent.

One aspect of this invention is the discovery that phenylcarbocyclic aryl alkenoic acid, and particularly 4-Phenyl-Δ3-transbutenoic acid compound can be used to modulate protein expression. For example, the particular compound has been shown to restore normal biosynthetic trafficking to the CFTR mutation ΔF508. Without wishing to be bound to theory, it is believed that the mechanism centers on butyrate-mediated down-regulation of the chaperone protein Hsc70.

It has been found that 4-Phenyl-Δ3-transbutenoic acid and 4-PBA both have a second potent ability to regulate gene and/or protein expression in a number of physiologic processes. For example, it has been reported that 4-PBA administration increases fetal hemoglobin levels, perhaps by transcriptional up-regulation. See Dover et al. supra and Stamatoyannopoulos et al., *Blood*, 84:3198-3204 (1994). Fetal hemoglobin levels and percent F cells increase, and it is thought that transcriptional upregulation of δglobin may be explained by the observation that butyrate promotes regulation of gene expression via inhibition of histone deacetylase. Inhibition of histone deacetylation by the butyrates is reported to be associated with tumor cell differentiation and is the rationale for the use of phenylbutyrate as a adjunct chemotherapeutic agent.

As discussed previously, the butyrate class of chemical agents including many of the compounds of this invention may be thought of as a new kind of "gene drug" that acts by transcriptional regulation. Transcriptional regulators can be harnesses to up or down-regulate redundant gene pathways that normally are relatively quiescent.

More particularly, a new class of chemical compound is disclosed herein which in particular embodiments can treat the ΔF508 trafficking defect through a pharmacologic strategy. One goal is the restoration of normal chloride conductance using a transcriptional regulator to correct the biosynthetic trafficking defect associated with ΔF508 expression and enhance the mutant protein chloride transport.

A preferred compound of this invention, 4-Phenyl-Δ3-transbutenoic acid (or trans styrylacetic acid), may be employed as a sole or adjunctive therapeutic agent for the treatment or prevention of the inherited urea cycle disorders as well as other maladies, e.g., inherited hemoglobinopathies, thalassemias and cancer. Buphenyl has been approved for use in some of these conditions. See Dover et al., *Blood*, 84:339-343 (1994); Dover et al., *N. Engl. J. Med.*, 327:569-570 (1992); Collins et al., *Blood*, 85:43-49 (1995); K. Smigel, *J. Natl. Cancer Inst.*, 84: 1398-1398 (1992); and Wood et al., *Proc. Annu. Meet. Am. Assoc. Cancer Res.*, 35: A2404 (1994). Ninety percent of administered 4-PBA is excreted as PAG in the urine. There is little toxicity beyond a slightly bitter taste, mild stomach discomfort or mild peripheral edema if severely anemic.

There have been substantial efforts to analyze protein degradation pathways. for example, the 70 kD heat shock protein family consists of Hsp70 (sometimes called Hsp72) which is inducible by heat shock and/or the presence of denatured intracellular proteins and Hsc70 (sometimes called Hsp73), the 70 kD heat shock cognate protein which is constitutively expressed and is involved in the uncoating of clathrin-coated endosomes. Hsc70 also has a role in the lysosomal degradation of intracellular proteins, and was recently shown to be required for the ubiquitin-dependent degradation of a number of cellular proteins. (Gething et al., *Nature*, 355:33-45 (1992) and Chiang et al., *Science*, 246:382-385 (1989) Since the rapid intracellular degradation of ΔF508 can be disrupted by the addition of ATP. (Strickland et al., *J. Biol. Chem.* 272: 25421-25424 (1997), which is known to regulate the association of proteins with Hsc70, we asked whether Hsc70 was affected by the butrates.

4-PBA has been reported to promote functional correction of cAMP-medicated chloride transport in CF airway epithelial cells (Rubenstein et al., *J. Clin. Invest.*, 100:2457-2465 (1997) and to increase chloride transport in nasal potential difference measurements of homozygous ΔF508 patients taking the drug for 1 week. (Rubenstein et al., *Am. J. Resp. Crit. Car Med.*, 157:484-490 (1998). Without wishing to be bound to theory, it is believed that two potential mechanisms of action are at play. The first involves the endoplasmic reticulum quality control pathway for removal of misfolded or mutant proteins. This model is exemplified by the following Examples 1-3.

The following General Comments and Examples 1-3 refer to use of 4-PBA. See also Rubenstein, R. C. and R. L. Zeitlan, (2000), supra; the disclosure of which is incorporated herein by reference. Each of the methods described in Examples 1-3 can be modified to accomadate one or more carbocyclic aryl alkenoic acid derivatives including stereoisomers of phenylcarbocyclic aryl alkenoic acid derivatives and specifically cis and trans isomers of 4-phenyl-3Δ-butenoic acid.

Use of 4-phenyl-3Δ-transbutenoic acid is shown below in Examples 4-13.

General Comments

The following materials and methods (numbered 1-7) were used as needed in the following Examples.

1. Cell culture. IB3-1 cells (38) were grown on uncoated tissue culture plasticware in a 5% CO2 incubator at 37° C., or at 25° C. as noted. Standard growth medium was LHC-8 (Biofluids, Rockville, Md.) supplemented with 5% fetal bovine serum (Sigma Chemical, St. Louis, Mo., or Biofluids). 100 U/ml penicillin-streptomycin (GIBCO BRL, Gaithersburg, Md.), 0.2 mg/ml Primaxim (Imipenim, Merck, West Point, Pa.), 80 μg/ml tobramycin (Eli Lilly, Indianapolis, Ind.), and 2.5 μg/ml Fungizone (Biofluids). Cells for control experiments were cultured under these routine conditions. Growth medium for the treated cells was composed of the indicated agent at indicated concentration added to the routine growth medium and incubated at 37° C. in a 5% CO2 incubator. We previously determined that 4-PBA maintains a constant concentration under these culture conditions for at least 2 days (30).

2. Antibodies. Rabbit anti-CFTR antiserum 181 (directed against CFTR amino acids 415-427 prior to the first nucleotide binding fold) was described previously (25). A rabbit polyclonal antiserum specific for Hsc70 (5) was a generous gifts of Drs. C. R. Brown and W. J. Welch (University of California at Sand Francisco). A rat monoclonal antibody specific for Hsc70, clone 1B5, was a generous gift of Dr. A. Laszlo (Washington University, St. Louis, Mo.). This antibody is also commercially available (Stressgen Biotechnologies, Victoria, BC, Canada). A mouse monoclonal antibody directed against Hsp90 (clone AC88) and a rabbit polyclonal antisera specific for Hsp40 and Hsp70 were purchased from Stressgen Biotechnologies. A mouse monoclonal antibody directed against calnexin (clone AF8) (18) was a generous gift of Dr. Michael Brenner (Harvard University). A mouse monoclonal antibody to Hdj2 (clone KA2A5.6) was from NeoMarkers (Union City, Calif.). Donkey anti-rabbit IgG-horseradish peroxidase conjugate and sheep anti-mouse IGG-horseradish peroxi-dase conjugates were purchased from Amersham (Arlington Heights, Ill.). Goat anti-rat IgG-horseradish peroxidase conjugate was purchased from Boehringer-Mannheim (Indianapolis, Ind.) or Amersham.

3. Immunoblot analysis. Whole cell lysates were prepared by solubilization with 2% SDS at 95° C. Protein concentration in the lysates was determined using the Bio-Rad DC assay reagents with bovine plasma g-globulin as a standard (Bio-Rad Laboratories, Hercules, Calif.). Equal amounts of protein was resolved on 5, 7, 8, or 9% SDS-polyacrylamide gels. Proteins were transferred to nitrocellulose, and immunodetection was performed as previously described (25). Nonspecific binding was blocked by incubation of the nitrocellulose with 2% gelatin or 10% nonfat day milk. Primary antisera and secondary antibodies were applied in buffer containing 0.4% BSA overnight at 4° C. and for 1 h at room temperature, respectively. Detection of immunoreactivity was performed with the enhanced chemiluminescence reagent (ECL, Amer-sham) and fluorography. Recombinant bovine Hsc70 (0.95% purity) was purchased from Stressgen Biotechnologies for use in constructing a standard curve of Hsc70 immunoreactivity. Immunoblots containing the bovine Hsc70 were probed with the Hsc70-specific polyclonal antiserum.

4. RNase protection. An Hsc70-specific probe for RNase protec-tion was constructed by isolation a 500-bp EcoR I fragment from American Type Culture Collection (ATCC) plasmid 77659 (ATCC, Manassas, Va.) and ligating this fragment into the EcoR I site of pSK(2) (Bluescript, Stratagene, La Jolla, Calif.). The resulting plasmid was sequenced in the Genetics Core Facility at the Johns Hopkins Hospital and found to be identical to sequences in exons 8 and 9 of the human Hsc70 sequence, with sequencing using the T3 primer and T7 primer leading to sense and antisense sequence, respectively. Hybridization probes were synthesized using a Maxiscript T7 kit (Ambion, Austin, Tex.) and [$\alpha^{32}$P]UTP (Amersham or DuPont NEN, Boston, Mass.) according to the Maxiscript protocol. Templates for internal control hybridizations, pTRI-18S and pTRI-cyclophilin A, were purchased from Ambion, and probes were similarly synthesized using the Maxiscript T7 kit. Probes were isolated by acid phenol-chloroform (Ambion) extraction, separated from unincorporated nucleotide by gel filtration (Sephadex G25 RNAspin column, Boehringer-Mannheim), and ethanol-acetate precipitated before resuspension in hybridization buffer. The concentration of radioactivity in the synthesized probes was determined by liquid scintillation.

RNase protection experiments were performed using the Direct Protect RNase protection assay kit (Ambion) according to the manufacturer's protocol. IB3-1 cell lysates were pre-pared in Direct Protect lysis buffer according to the manufacturer's protocol after incubation under the appropriate conditions for 48 h. Probe (50-70 and 5-10 thousands of counts/min for Hsc70 and control, respectively) and cellular RNA were hybridized overnight at 37° C. and digested with RNase cocktail. Protected fragments were resolved by electrophoresis on 5% acrylamide-8 M urea gels and detected by fluorography. Hsc70 mRNA concentration is expressed relative to control (18S or cyclophilin A) hybridization by densitometry (see *Densitometric analysis*). Results for hybridization of Hsc70 mRNA relative to the two control species were similar and were therefore grouped for data analysis.

5. Immunoprecipitation. Cultured cells were solubilized by incubation for 1 h at 4° C. in RIPA[50 mM Tris-Cl (pH8.0), 150 mM NaCl, 1% Triton X-100 (Bio-Rad or Fisher Scientific), 1% sodium deoxycholate (Sigma), and protease inhibitor cocktail (Sigma; used at 1:1,000 final dilution)]. Solubilized cells were then homogenized by passage 10 times through a 20-gauge needle and cleared by centrifugation at 15,000 g for 20 min at 4° C. Protein concentration was determined using the Bio-Rad DC reagents as above. Polyclonal Hsc70 antiserum was added to the cell lysates (2 µl/250 µg total protein, with equal amounts of protein at equal final concentrations for each condition within an experiment) and incubated at 4° C. over-night with gentle agitation. Immune complexes were captured with protein A-Sepharose 4B (Pharmacia Biotechnologies, Piscataway, N.J.) that had been preabsorbed with BSA for 45 min at 4° C. Precipitated complexes were collected by centrifugation and washed twice with cold RIPA and twice with cold TBS (50 mM Tris-Cl, pH 7.6, and 150 mM NaCl). Immunoprecipitated protein was related from the beads by incubation in SDS-PAGE sample buffer for 1 h at 70° C. and resolved on 5 or 7% SDS-polyacrylamide gels. Immunodetection of immunoprecipitated Hsc70 or CFTR was performed as described above.

6. Densitometric analysis. Fluorographic images were digitized using an AlphaImager 2000 digital analysis system (AlphaInnotech, San Leandro, Calif.). Densitometric analysis of these images were performed using AlphaImager image analysis software (version 4.0. AlphaInnotech) with two-dimensional integration of the selected band. Density of the lane surrounding the band was similarly determined by two-dimensional integration and used as a baseline density for background subtraction. for comparisons within an experiment, the density of the control lane, the 100-ng lane for bovine Hsc70 standard curve experiments and the 10-µg lane for CFTR standard curve experiments, was arbitrarily set to 1.0. A one-way ANVOA was used to determine statistical significance of changes in density of fluorographic bands (SPSS software, version 7.0).

7. Reagents. Pharmaceutical grade 4-PBA, manufactured by Triple Crown America (Perkasie, Pa.), was a gift of Dr. Saul Brusilow (Johns Hopkins School of Medicine). The sources for other reagents were as follows: reagent grade butyric acid and phenylacetic acid, Sigma; ACS reagent grade glycerol, J. T. Baker (Phillipsburg, N.J.) or Fisher; Geneticin (G418), GIBCO BRL; nitrocellulose, Schleicher & Schuell (Keene, N.H.) or Amersham. Electrophoresis grade chemicals were obtained from Fisher, Bio-Rad, or GIBCO BRL. All other reagents were of reagent grade or better.

All documents mentioned herein are incorporated by reference herein in their entirety.

The present invention is further illustrate by the following non-limiting examples.

EXAMPLE 1

4-PBA Treatment of IB3-1 Cells Decreases Expression of Hsc70

In this example the immortalized cystic fibrosis bronchiolar epithelial cell line IB3-1 (38). IB3-1 has the CFTR genotype ΔF508/W1282X and is a model system for study of the intracellular trafficking of ΔF508-CFTR because the W1282X allele gives rise to an unstable and therefore untranslated mRNA. This results in IB3-1 cells containing only ΔF508-CFTR (17). It has been shown that treatment of IB3-1 cells with 4-PBA results in restoration of appropriate intracellular trafficking of ΔF508-CFTR (30).

Figure 1B:
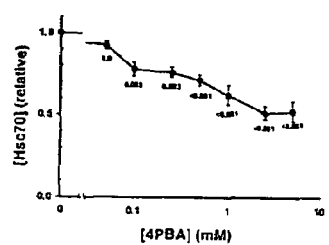
FIG. 1B is a graph showing densitometery of results from immunoblot experiments in which relative heat shock protein 70 (hsc70) levels are determined versus mM 4-PBA.
Figure 1C:
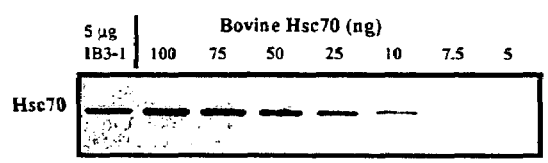
FIG. 1C is a representation of a Western Blot showing a standard curve construction.
Figure 1D:
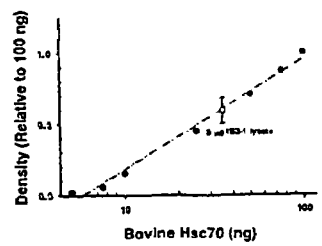
FIG. 1D is a graph showing densitometery of results from immunoblot experiments in which relative hsc70 levels determined versus bovine hsc70.
Figure 2A:
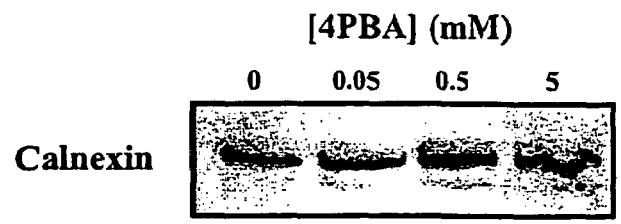
FIG. 2A-E are Western Blots showing amounts of Calnexin (FIG. 2A), various heat shock proteins (FIGS. 2B-D) and Hdj2 (FIG. 2E) in the presence of mM 4-PBA.
Figure 2B:
Figure 2C:
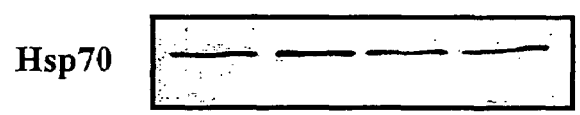
Figure 2D:
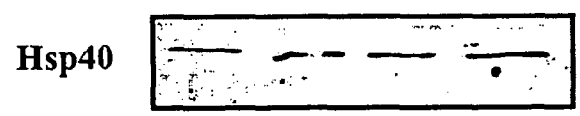
Figure 2E:
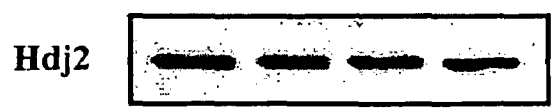

IB3-1 cells were treated with increasing concentrations of 4-PBA in culture for 2 days. As shown in FIG. 1, total Hsc70 immunoreactivity in whole cell lysates declined in a dose-dependent fashion with increasing concentrations of 4-PBA as detected by a Hsc70-specific rabbit polyclonal antiserum (FIG. 1A, representative immunoblot; FIG. 1B, compiled densitometric analysis of FIG. 1A and 7 other immunoblots). Similar data were obtained when a rat monoclonal antibody to Hsc70 was used to probe the immunoblots. These data are consistent with 4-PBA inducing a dose-dependent reduction of cellular Hsc70 protein. To estimate the decrease in Hsc70 protein represented by this, 50% decrease in immunoreactivity, a densitometric standard curve of immunoreactivity was constructed for recombinant bovine Hsc70 (FIG. 1C, representative immunoblot; FIG. 1D, standard curve derived from FIG. 1C and two other experiments).

Log and linear regressions for the data of FIG. 1D were performed, and both were acceptable fits (r 2 for log and linear were 0.973 and 0.930, respectively). The superiority of the log fit may be due to saturation of the X-ray film used for fluorography at high amounts of Hsc70, although the densitometer was still able to distinguish density variation. These data suggest that IB3-3 cells contain 35 ng Hsc70/5 µg total cellular protein. Furthermore, these data demonstrate a good correlation of Hsc70 immunoreactivity and measured densitometry; a 50% decrease in measured density corresponds to an, 50-60% decrease in total Hsc70 protein immunoreactivity.

Whether 4-PBA would regulate expression of a number of other molecular chaperones in IB3-1 cells (FIG. 2) was assessed next. Calnexin is a molecular chapter one present in the ER membrane that binds to glycoproteins in the ER via high-mannose core residues and has previously been shown to have a prolonged interaction with ΔF508-CFTR in heterologous cells expressing ΔF508-CFTR (28). Hsp90 is required for correct folding and function of a number of cellular proteins (16). Inhibition of Hsp90 function with geldanamycin leads to more rapid degradation of ΔF508-CFTR (24), suggesting that Hsp90 may be required for CFTR trafficking. Hsp70 (Hsp72) expression is induced by heat shock and the presence of denatured proteins within the eukaryotic cell (16). In *Escherichia coli,* the Hsp70 homologue DnaK and the Hsp40 homologue DnaJ act to promote protein folding (16). Hdj2 is the member of the Hsp40 family that specifically interacts with and regulates the ATPase activity of Hsc70. Hdj2 also interacts with CFTR during CFTR translation (26). Increasing concentrations of 4-PBA did not affect the expression of calnexin, Hsp90, Hsp70, Hsp40, or Hdj-2 in IB3-1 cells.

To substantiate these observations, densitometric analysis of the representative immunoblots of FIG. 2 and similar separate experiments (n 53 independent experiments for each chaperone including intermediate concentrations of 4-PBA) was performed. These data and the data of FIG. 1 are consistent with selective regulation of only Hsc70, the constitutively expressed member of the 70-kDa heat shock protein family by 4-PBA, and none of the other five molecular chaperones assessed.

FIGS. 1A-C are more specifically explained as follows. FIG. 1. Dose-dependent reduction in Hsc70 expression mediated by sodium 4-phenylbutyrate (4-PBA). A: IB3-1 cells were incubated with indicated concentration of 4-PBA for 48 h. Whole cell lysates were prepared with SDS as described under General Comments. Total protein (5 µg) was resolved on 8% SDS-polyacrylamide gels. Proteins were electrophoretically transferred to nitrocellulose, and immunodetection of Hsc70 was performed as described under General Comments. Primary antiserum was rabbit polyclonal antiserum specific for Hsc70. B: densitometry was performed as described under General Comments on 8 total immunoblot experiments (4 experiments performed in duplicate). Density of 0 4-PBA (control) lane was set to 1, and density (means 6 SE) of other lanes is expressed relative to control. Statistical significance (P values indicated below error bars) was determined by a 1-way ANOVA in comparison with control. C; standard curve construction. IB3-1 lysate protein (5 µg) or indicated amount of purified recombinant bovine Hsc70 was resolved on 8% SDS-polyacrylamide gels. Proteins were electrophoretically transferred to nitrocellulose, and immunodetection of Hsc70 was performed as described above under General Comments. Primary antiserum was rabbit polyclonal antiserum specific for Hsc70. D: densitometry was performed as described under General Comments on 3 identical experiments. Density of 100-ng lane was set to 1, and densities of other lanes are expressed relative to 100-ng lane. Mean relative density is shown by filled circles. Error bars (SE) are contained within symbols. Relatively density of 5 µg of IB3-1 lysate is depicted by open circle and corresponds to about 35 ng of bovine Hsc70 immunoreactivity.

FIGS. 2A-2E are more specifically explained as follows. Calnexin, Hsp90, Hsp70, Hsp40, and Hdj2 expression is unchanged by 4-PBA treatment. IB3-1 cells were treated as described for FIG. 1. Immunoblotting with 5 µg of IB3-1 SDS lysate protein was performed as described in the foregoing General Comments.

EXAMPLE 2

4-PBA Treatment Results in Decreased Hsc70 mRNA Expression

Because 4-PBA is known to regulate transcription, whether the concentration-dependent decrease in Hsc70 protein expression was reflective of a decrease in Hsc70 mRNA expression was examined next. Hsc70 mRNA was measured in lysates of IB3-1 cells by RNase protection. It was found that, in comparison to levels of 18S rRNA as an internal standard for total RNA assayed and recovered, a concentration-dependent decrease in steady-state Hsc70 mRNA levels after 4-PBA treatment (FIG. 3) that correlated with the decrease in Hsc70 immunoreactivity observed in FIG. 1. There was a maximum decrease of, 50% of control expression with continuous exposure to 5 mM 4-PBA.

Figure 3A:
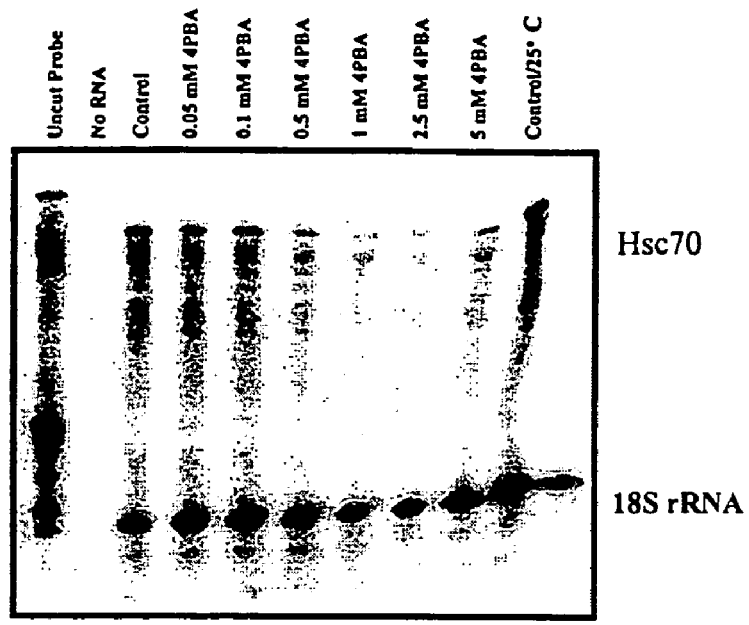
FIG. 3A is a representation of a gel showing results of an RNase protection experiment using an hsc70 probe.
Figure 3B:
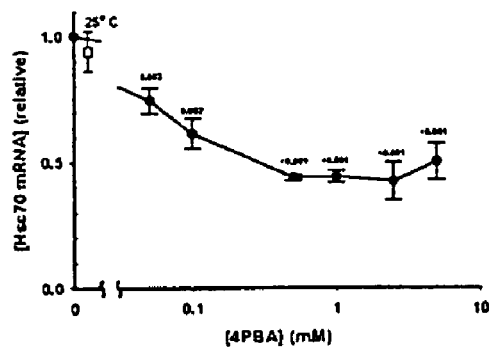
FIG. 3B is a graph showing densitometry results of RNase protection experiments in which relative hsc70 amounts are compared to mM 4-PBA.

FIGS. 3A-B are explained in more detailed as follows. Dose-dependent downregulation of Hsc70 mRNA expression by 4-PBA. A: IB3-1 cells were treated as for FIGS. 1 and 2. Hsc70 mRNA and 18S rRNA (as an internal reference) were measured by Direct Protect RNase protection as described under General Comments. B: densito-metric analysis on 3 independent experiments was performed as described by first normalizing density of Hsc70 hybridization by internal reference RNA hybridization (either 18S rRNA or cyclophilin A mRNA hybridization; see General Comments) to control for total RNA in each hybridization and RNA recovery during assay. This ratio for each condition was subsequently made relative to Hsc70-to-reference RNA ratio for control lane. Means 6 SE for 3 independent experiments are shown. P values (shown above respective error bars) were determined by 1-way ANOVA in comparison with control.

EXAMPLE 3

Figure 4A:
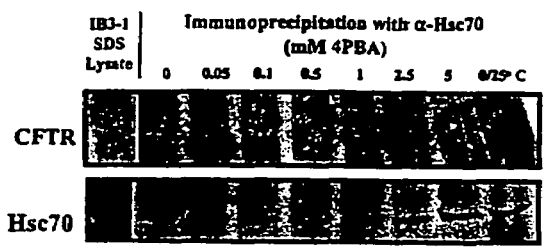
FIG. 4A is a representation of a Western Blot showing results of immunoprecipitation with an anti-hsc70 antibody.

ΔF508-CFTR Forms a Complex with Hsc70 that is Decreased by 4-PBA, Low Temperature, Butyrate, and Glycerol Immunoprecipitation with an antiserum that recognizes both Hsp70 and Hsc70 results in the coimmunoprecipitation of ΔF508-CFTR (37). A direct interaction between CFTR and Hsc70 was confirmed by testing whether specific immunoprecipitation of Hsc70 would result in coimmunoprecipitation of CFTR immunoreactivity (FIG. 4A). The relative mobility of CFTR in this experiment was ~170 kDa, which is consistent with the ER glycosylated "band B" form. Recovery of Hsc70 by immunoprecipitation was ~10% of input, which is typical in this kind of experiment when recovery has been measured (26). It is assumed that this is representative of the total cellular pool of Hsc70.

As expected from the immunoblot data of FIG. 1, IB3-1 cells treated with increasing concentrations of 4-PBA had decreased amounts of immunoprecipitable Hsc70 (FIG. 4A). With increasing concentrations of 4-PBA, less immunoreactive CFTR was recovered in complex with Hsc70. At >1 mM 4-PBA, CFTR was undetectable in the immunoprecipitates. Similarly, CFTR was not associated with Hsc70 when IB3-1 cells were incubated at 25° C. We previously showed that treatment with >0.1 mM 4-PBA or incubation at 25° C. leads to increased overall expression and the appearance of mature CFTR in IB3-1 cells (30). To better quantify this change, densitometric analysis was performed of this and similar experiments (FIG. 4B) and constructed a densitometric standard curve of CFTR immunoreactivity using IB3-1 lysate protein (FIG. 4C). The standard curve suggests that CFTR immunoreactivity as detected by densitometry decreases linearly as a function of decreasing protein but that the decrease in densitometric signal exceeds the decrease in CFTR protein, i.e., a decrease in IB3-1 protein from 5 to 2.5 µg leads to an approximately two-thirds decrease in densitometric signal. CFTR immunoreactivity was not consistently detected in samples containing 2 µg of IB3-1 protein and was not detected in samples containing 1 µg of IB3-1 protein. Thus the slightly greater change in CFTR vs. Hsc70 densitometric signal in FIG. 4B actually reflects a similar decrease in immunoreactive protein of the two species.

Figure 4B:
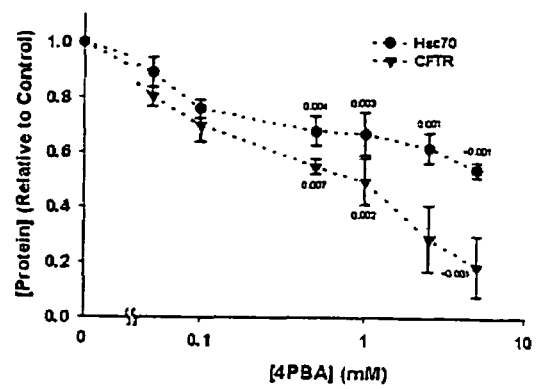
FIG. 4B is a graph showing densitometery results of protein relative to control in the presence of mM 4-PBA.
Figure 4C:
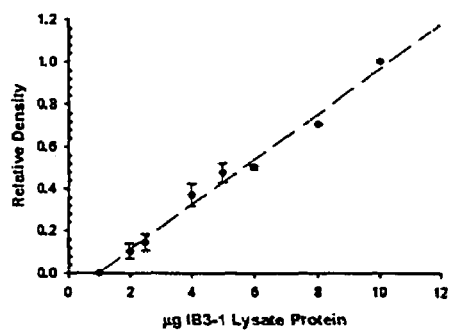
FIG. 4C is a graph showing densitometery results of a CFTR standard curve construction.

FIGS. 4A-C are more specifically explained as follows. 4-PBA-treatment of IB3-1 cells decreases amount of cystic fibrosis transmembrane conductance regulator (CFTR) immunoreac-tivity coprecipitated with Hsc70. IB3-1 cells were grown in indicated concentration of 4-PBA for 2 days at 37° C. Cells were solubilized with RIPA, and 250 µg of total protein were incubated with Hsc70-specific rabbit polyclonal antiserum as described under General Comments. Immune complexes were recovered by centrifugation after incubation with protein A-Sepharose. Composition of precipitated immune complexes was analyzed by SDS-PAGE and protein immunoblot using anti-CFTR antiserum 181 and rabbit polyclonal anti-Hsc70 antibody as de-scribed under General Comments. Total protein (10 µg) was resolved in IB3-1 SDS lysate lane, and immunoprecipitate from equivalent of 80 µg of cellular protein was analyzed in immunoprecipitation lanes. Relative mobility of CFTR associated with Hsc70 was, 170 kDa. B: densitometric analysis of these and similar immunoblots (4 independent experiments) was performed as described for FIG. 1. Mean density (6SE) relative to control values for 4 independent experiments is shown. P values vs. control were determined by 1-way ANOVA. C: CFTR densitometry standard curve construction. Immunodetection of CFTR in indicated amount of IB3-1 lysate protein was performed as described under General Comments. Densitometry was performed as described as described above on 4 independent concentration curves. For each independent experiment, density of CFTR immunoreactivity in 10-µg sample was set to 1, and densities of CFTR immunoreactivity in other samples are expressed relative to 10-µg lane. Mean relative density is shown by closed symbols. Error bars (SE) are contained within symbols where no visible.

The decrease in CFTR recovered by immunoprecipitation in proportion to the decrease in Hsc70 is consistent with 4-PBA not directly influencing the binding affinity of CFTR and Hsc70. This was further assessed by immunoprecipitating Hsc70-CFTR complexes from untreated IB3-1 cells either with or without 1 mM 4-PBA added to the RIPA lysis and wash buffers. The recovery of Hsc70 and associated CFTR was unaltered in the presence of 4-PBA which is consistent with 4-PBA not altering the in vitro affinity of Hsc70 for CFTR.

Collectively, these data suggest that 4-PBA treatment leads to an increased proportion of ΔF508-CFTR escaping association with Hsc70 due to a decrease in Hsc70 expression. If association with Hsc70 is necessary for CFTR ubiquitination, as it is for a number of other cellular proteins (3), then escape from this association may decrease the proportion of ΔF508-CFTR that is prematurely degraded.

Next, effects of two compounds that promote trafficking of ΔF508-CFTR to the plasma membrane, the transcriptional regulator butyrate (9) and the chemical chaperone glycerol (4, 30, 33). Also tested was the major in vivo metabolite of 4-PBA, phenylacetate, and the aminoglycoside antibiotic geneticin (G418). G418 promotes read through and stabilization of the otherwise unstable mRNA derived from the W1282X missense allele present in IB3-1 cells and results in the appearance of CFTR channel activity at the IB3-1 plasma membrane (2). Representative data for these immunoblot experiments are shown in FIG. 5. The results again demonstrate a reduction in Hsc70 immunoreactivity with 1 mM butyrate and 1M glycerol but not change in Hsp90, Hsp70, or Hsp40 immunoreactivity.

Figure 5A:
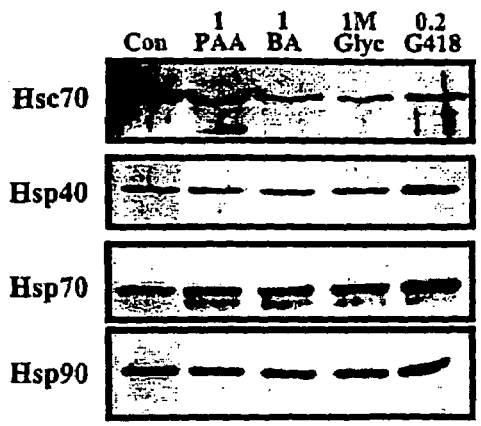
FIG. 5A shows representation of Western blots analyzed for presence of hsc70 using a polyclonal serum.
Figure 5B:
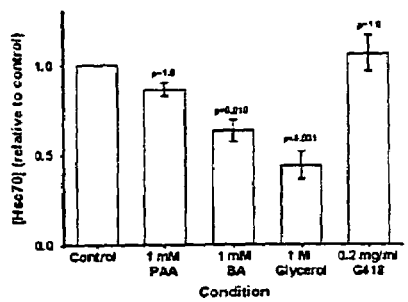
FIG. 5B is a graph showing densitometric results of hsc70 expression under various conditions and relative to a control.
Figure 5C:
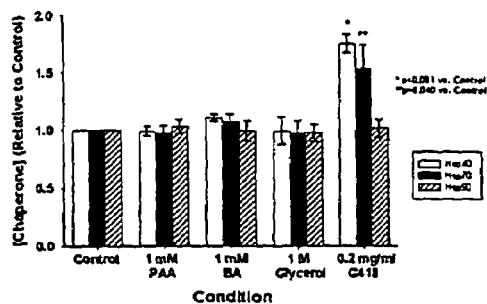
FIG. 5C is a graph showing densitometric results of chaperone under various conditions and relative to a control.

FIGS. 5A-C are explained in more detail as follows. Hsc70 expression in IB3-1 cells is decreased by butyrate (BA; 1 mM) and glycerol (Glyc, 1 M) but not phenylacetate (PAA; 1 mM) and G418 (0.2 mg/ml); Hsp90, Hsp70, and Hsp40 expression are not affected by these agents. A: IB3-1 cells were incubated at 37° C. for 2 days under indicated conditions. Cellular homogenates were prepared in 2% SDS as described in METHODS, and 5 µg of total cellular protein were analyzed by immunoblot for Hsc70 using rabbit polyclonal antiserum, Hsp90, Hsp70, Hsp40 as described above under General Comments. Con, control. B and C: densitometric analysis of Hsc70 expression (B) and Hsp90, Hsp70, and Hsp40 expression (C) was performed as described for FIG. 1. B: means 6 SE of density in 4 independent experiments. C: means 6 SE of relative density in 3 (Hsp70) or 4 (Hsp40 and Hsp90) independent experiments. P values vs. control (B and C) were determined by 1-way ANOVA.

These observations are consistent with the hypothesis that conditions that promote ΔF508-CFTR trafficking to the cell surface are associated with a reduction in Hsc70 expression, al-though we have yet to establish a causal relationship. Phenylacetate at 1 mM had little effect on Hsc70 or Hsp90 expression. In vivo, 4-PBA is rapidly and completely converted by β-oxidation to phenylacetate and then conjugated with glutamine to form phenacetylglutamine, which is excreted in the urine (6). Phenylacetate has a different potency profile from butyrate or 4-PBA with respect to specific gene induction (8). These results suggest that 4-BPA alone may regulate Hsc70 expression. G418, which acts on the W1282X allele and not ΔF508-CFTR, had little effect on Hsc70 or Hsp90 but increased Hsp40 and Hsp70 immunoreactivity. Although it seems logical that increased Hsc70 might lead to reduced trafficking of CFTR derived from the W1282X allele, the W1282X-derived CFTR would have wild-type structure in the region of F508, and the F508 region may be a critical determinant of CFTR affinity for Hsc70.

Figure 6A:
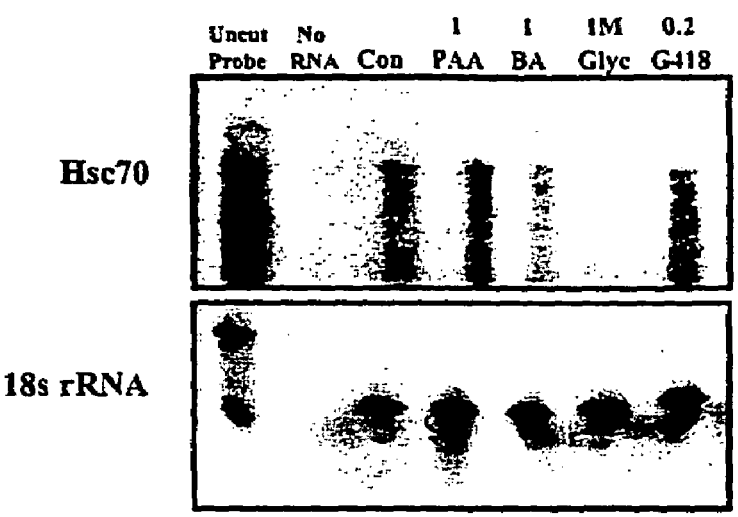
FIG. 6A is a representation of a Western Blot showing RNase protection results for hsc70 and 18s rRNA under various conditions.
Figure 6B:
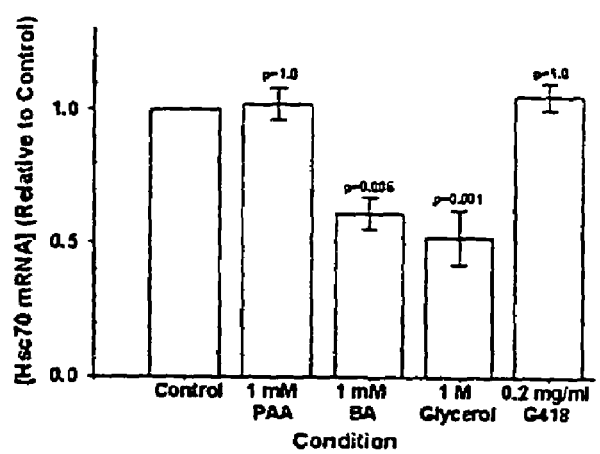
FIG. 6B is a graph showing densitometric results of hsc70 mRNA relative to control under various conditions.
Figure 7A:
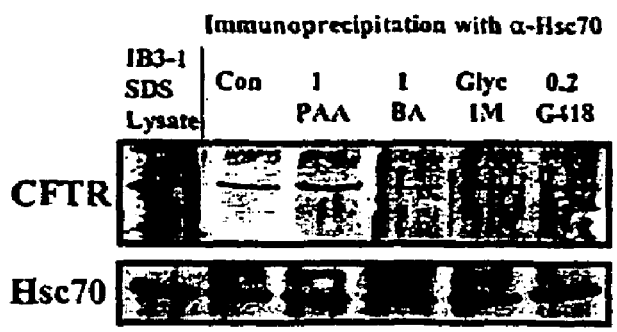
FIG. 7A is a representation of a Western Blot showing the cystic fibrosis transmembrane regulator (CFTR) and hsc70 expression under various conditions.
Figure 7B:
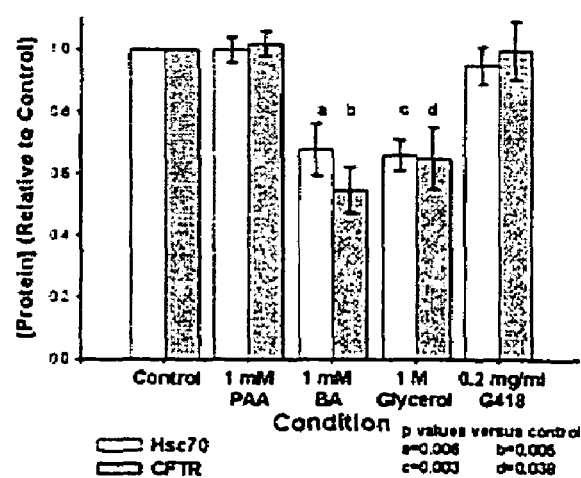
FIG. 7B is a graph showing densitometric results of hsc70 and CFTR protein under various conditions.

These changes in Hsc70 protein expression again correlated with changes in steady-state Hsc70 mRNA expression, as determined by RNase protection (FIG. 6). In this experiment, 1 mM butyrate and 1 M glycerol were associated with, 50% reduction in steady-state Hsc70 mRNA levels. The glycerol effect was unexpected and may occur by a mechanism different from that of the butyrates. Results as shown in FIG. 5 predict that conditions that do not affect Hsc70 expression would allow CFTR to associate with Hsc70. We tested this prediction by coimmunoprecipitation. FIG. 7 demonstrates the treatment of IB3-1 cells with glycerol or butyrate decreases the amount of immunoreactive CFTR copre-cipitated with Hsc70. Again, the densitometric analysis of this and similar experiments (FIG. 7B) suggests that the decrease in CFTR associated with Hsc70 resulted from decreased expression of Hsc70.

FIG. 6 is explained in more detail as follows. Butyrate and glycerol also decrease Hsc70 mRNA expression. A: IB3-1 cells were incubated under indicated conditions for 2 days before preparation of cellular lysates for assay of Hsc70 mRNA and control RNA (18S rRNA) by Direct Protect RNase protection as described above. B: densitometric analysis was performed as described for 4 independent experiments by first normalizing density of Hsc70 hybridization to reference RNA hybridization (18S rRNA or cyclophilin A mRNA) to control for total RNA in each hybridization and RNA recovery during the assay. This ratio for each condition was subsequently made relative to Hsc70-to-reference RNA ratio for control lane. Plotted are means 6 SE relative Hsc70 mRNA expression for 4 independent experiments. P values (shown above respective error bars) were determined by 1-way ANOVA in comparison with control.

FIG. 7 is more specifically explained as follows. Butyrate and glycerol treatment of IB3-1 cells decreases amount of CFTR immunoreactivity coprecipitated with Hsc70. A: IB3-1 cells were grown in indicated concentration of 4-PBA for 2 days at 37° C. Cells were solubilized with RIPA, and 250 ∝g of total protein were incubated with Hsc70-specific rabbit polyclonal antiserum as described under General Comments above. Immune complexes were recovered by centrifugation after incubation with protein A-Sepharose. Composition of precipitated immune complexes was analyzed by SDS-PAGE and protein immunoblot using anti-CFTR antiserum 181 and rabbit polyclonal anti-Hsc70 antibody as described above. Total protein (10 μg) was resolved in IB3-1 SDS lysate lane, and immunoprecipitate from equivalent of 80 μg of cellular protein was analyzed in immunoprecipitation lanes. Relative mobility of CFTR coimmunoprecipitated with Hsc70 was again, 170 kDa. B: denistometric analysis of these immunoblots (4 independent experiments) was performed as described for FIG. 1. Shown is mean density (6SE) relative to control for 4 independent experiments. P values vs. control were determined by 1-way ANOVA.

These data are consistent with a model in which a gents that improve ΔF508-CFTR intracellular trafficking decrease the total amount of ΔF508-CFTR/Hsc70 complex. There was little effect of phenylacetate or G418 treatment. The latter observation is consistent with G418 acting by a mechanism different from that of 4-PBA, glycerol, or butyrate. This is also consistent with G418 acting on the W1282X-CFTR allele present in IB3-1 and not on the ΔF508 allele that is the target of 4-PBA glycerol, or butyrate.

Specific Comments

The foregoing Examples show that 4-PBA, which was previously shown to facilitate trafficking of ΔF508-CFTR to the plasma membrane (30), downregulates Hsc70 at the protein and mRNA levels. Consistent with these findings was the reduction in ΔF508-CFTR/Hsc70 complexes. Similar effects on Hsc70 protein and mRNA expression and ΔF508-CFTR/Hsc70 complex formation were observed for butyrate and glycerol, both of which restore ΔF508-CFTR trafficking. Interaction with Hsc70 is thought to be a key step in targeting a number of cellular proteins for ubiquitination and degradation by the proteasome (3). The usual intracellular fate of ΔF508-CFTR is degradation, at least in part by the ubiquitin-proteasome system (20, 36). Therefore, 4-PBA may promote ΔF508-CFTR trafficking by inhibiting its recognition by the intracellular degradation pathway.

The decrease in Hsc70 protein expression induced by 4-PBA, butyrate, and glycerol is, 40-60%. These data are consistent with observations that small perturbations in Hsc70 expression can result in alterations in cellular function. Butyrate is typically thought to act as a transcriptional activator, which contrast with these examples. However, decreased expression of surfactant proteins A and B mRNA in fetal rat lung has been reported in response to butyrate treatment (27). This is consistent with the examples suggesting a decrease in Hsc70 expression at the protein and mRNA levels after treatment with butyrate and 4-PBA.

Δ508-CFTR is typically degraded by the ubiquitin-proteasome system (20, 36). However, inhibition of the proteolytic component of this system with lactacystin or N-acetyl-L-leucinyl-L-leucinyl-L-leucinyl-L-leucinal does not promote ΔF508-CFTR trafficking to the cell surface (20, 36). These observations suggest that the committed step for intracellular degradation occurs earlier in the pathway than the actual proteolysis.

Hsc70 associates with CFTR during CFTR translation, and the association with ΔF508-CFTR is greater and longer lived than with wild-type CFTR (26). CFTR also undergoes cotranslational ubiquitination (32), and the possibility of enhanced ubiquitin-dependent degradation of the ΔF508 peptide in the presence of Hsc70 is absent in the in vitro folding system (34). Collectively, these data are consistent with a model in which Hsc70 remains associated with species that are "partially structured" and likely to aggregate, thereby preventing aggregation. The foregoing Examples are consistent with, at most, a 40-60% reduction in Hsc70 expression at clinically relevant 4-PBA concentrations.

A working model is suggested by these Examples. Under physiological conditions, <1% of ΔF508-CFTR is trafficked via the normal pathway; >99% is targeted for and subsequently degraded (35). In contrast, only, ~75% of wild-type CFTR is targeted for and subsequently degraded, whereas 25% of wild-type CFTR is trafficked to the cell surface (35). Based on these proportions, the "trafficking" pathway for ΔF508-CFTR is disfavored by at least 2-3 kcal/mol compared with that of wild-type CFTR (7). This results from either an intrinsic instability of the ΔF508-CFTR protein, as is suggested by the higher proportion of ΔF508-CFTR that would enter the degradative pathway compared with wild-type CFTR.

In this working model, decreasing the association of ΔF508-CFTR with the recognition protein would promote its trafficking to the cell surface. The observed decrease in Hsc70 recovered by immunoprecipitation in FIG. 4 could also contribute to this effect. Decreasing the intracellular concentration of the recognition protein, such as Hsc70, by, ~50% would similarly decrease its rate of association with ΔF508-CFTR and lead to a reduction in premature degradation of ΔF508-CFTR. More newly synthesized ΔF508-CFTR would thereby enter the trafficking pathway.

The foregoing Examples have shown that 4-PBA and butyrate decrease both the expression of Hsc70 mRNA and protein and also its association with ΔF508-CFTR. These date are consistent with a hypothetical model in which the association of ΔF508-CFTR with Hsc70 leads to ubiquitination and proteasomal degradation of ΔF508-CFTR. 4-PBA- and butyrate-mediated reduction in Hsc70 may promote ΔF508-CFTR trafficking to the cell surface.

The following references 1-38 are referred to by number under the General Comments, Examples 1-3 and Specific Comments sections provided above. The disclosures of each reference are incorporated herein by reference in their entirety.

1. Aquino, D. A., D. Peng, C. Lopez and M. Farooq. The constitutive heat shock protein-70 is required for optimal expression of myelin basic protein during differentiation of oligodendro-cytes. *Neurochem. Res.* 23: 413-420, 1998.
2. Bedwell, D. M., A. Kaenjak, D. J. Benos, Z. Bebok, K. Bubien, J. Hong, A. Tousson, J. P. Clancy, and E. J. Sorscher. Suppression of a CFTR premature stop mutation in a bronchial epithelial cell line. *Nat. Med.* 3: 1280-1284, 1997.
3. Bercovich, B., I. Stancovski, A. Mayer, N. Blumenfeld, A. Laszlo, A. L. Schwartz, and A. Ciechanover. Ubiquitin-dependent degradation of certain protein substrates in vitro requires the molecular chaperone Hsc70, *J. Biol. Chem.* 272: 9002-9010, 1997.
4. Brown, C. R., L. Q. Hong-Brown, J. Biwersi, A. S. Verkman, and W. J. Welch. Chemical chaperones correct the mutant phenotype of the DF508 cystic fibrosis transmembrane conductance regulator protein. *Cell Stress Chaperones* 1: 117-125, 1996.
5. Brown. C. R., R. L. Martin, W. J. Hansen, R. P. Beckmann, and W. J. Welch. the constitutive and stress inducible forms of hsp70 exhibit functional similarities and interact with one another in an ATP-dependent fashion. *J. Cell Biol.* 120: 1101-1112, 1993.
6. Brusilow, S. W. Phenylacetylglutamine may replace urea as a vehicle for waste nitrogen excretion. *Pediatr. Res.* 29: 147-150, 1991.
7. Castellan, G. W. *Physical Chemistry.* Reading, Mass.: Addison-Wesley, 1971.
8. Chen, W. Y., E. C. Bailey, S. L. McCune, J. Y. Dong, and T. M. Townes, Reactivation of silenced, virally transduced genes by inhibitors of histone deacetylase. *Proc. Natl. Acad. Sci. USA* 94: 5798-5803, 1997.
9. Cheng, S. H., S. L. Fang, J. Zabner, J. Marshall, S. Piraino, S. C. Schiavi, D. M. Jefferson, M. J. Welsh, and A. E. Smith. functional activation of the cystic fibrosis trafficking mutant DF508-CFTR by over expression. *Am. J. Physiol. Lung Cell. Mol. Physiol.* 268: L615-L624, 1995.
10. Cheng, S. H., R. J. Gregory, J. Marshall, S. Paul, D. W. Souza, G. A. White, C. R. O'Riordan, and A. E. Smith, Defective intracellular transport and processing of CFTR is the molecular basis of most cystic fibrosis. *Cell* 63: 827-834, 1990.
11. Chiang, H.-L., S. R. Terlecky, C. P. Plant, and J. F. Dice. A role for a 70-kilodalton heat shock protein in lysosomal degradation of intracellular proteins. *Science* 246: 282-385, 1989.
13. De la Rosa, E. J., E. Vega-Nunez, A. V. Morales, J. Serna, E. Rubio, and F. de Pablo, Modulation of the chaperone heat shock cognate 70 by embryonic (pro)insulin correlates with prevention of apoptosis. *Proc. Natl. Acad. Sci. USA* 95: 9950-9955, 1998.
14. DeLuca-Flaherty, C., D. B. McKay, P. Parham, and B. L. Hill. Uncoating protein (hsc70) binds a conformationally labile domain of clathrin light chain LCa to stimulate ATP hydrolysis. *Cell* 62: 875-887. 1990.
15. Denning, G. M., M. A. Anderson, J. F. Amara, J. Marshall, A. E. Smith, and M. J. Welsh. Processing of mutant cystic fibrosis transmembrane regulator is temperature-sensitive. *N-ture* 358: 761-764, 1992.
16. Gething, M.,-J., and J. Sambrook. Protein folding in the cell *Nature* 355: 33-45, 1992.
17. Hamosh, A., B. J. Rosenstein, and G. R. Cutting. CFTR nonsense mutations G542X and W1282X associated with severe reduction of CFTR mRNA in nasal epithelial cells. *Hum. Mol. Genet.* 1: 542-544, 1992.
18. Hochstenbach, F., V. David, S. Watkins, and M. B. Brenner, Endoplasmic reticulum resident protein of 90 kilodaltons associates with the T- and B-cell antigen receptors and major histocom-patibility complex antigens during their assembly. *Proc. Natl. Acad. Sci. USA* 89: 4734-4738, 1992.
19. Hyde, S. C., S. E. Smyth, D. C. Gruenert, and D. R. Gill. The effects of 4-phenylbutyric acid on CFTR mRNA levels (Abstract). *Pediatr. Pulmonol. Suppl.* 17: 211, 1998.
20. Jensen. T. J., M. A. Loo, S. Pind, D. B. Williams, A. L. Goldberg, and J. R. Riordan. Multiple proteolytic systems, including the proteasome, contribute to CFTR processing. *Cell* 83: 129-135, 1995.
21. Jiang, C., S. L. Fang, Y. F. Xiao, S. P. O'Connor, S. G. Nadler, D. W. Lee, D. M. Jefferson, J. M. Kaplan, A. E. Smith, and S. H. Cheng. Partial restoration of cAMP-stimulated CFTR chloride channel activity in DF508 cells by deoxyspergualin. *Am. J. Physiol. Cell Physiol.* 275: C171-C178, 1998.
22. Kartner, N., O. Augustinas, T. J. Jensen, A. L. Naismith, and J. R. Riordan. Mislocationzation of DF508 CFTR in cystic fibrosis sweat gland. *Nat. Genet.* 1: 321-327, 1992.
23. Krebs, C. J., E. D. Jarvis, and D. W. Pfaff. The 70-kDa heat shock cognate protein (Hsc73) gene is enhanced by ovarian hormones in the ventromedial hypothalamus. *Proc. Natl. Acad. Sci. USA* 96: 1686-1691, 1999.
24. Loo, M. A., T. J. Jensen, L. Cui, Y. Hou, X. B. Chang, and J. R. Riordan. Perturbation of Hsp90 interaction with nascent CFTR prevents its maturation and accelerates its degradation by the proteasome. *EMBO J.* 17: 6879-6887, 1998.
25. McGrath, S. A., A. Basu, and P. L. Zeitlin. Cystic fibrosis gene and protein expression during fetal lung development. *Am. J. Respir. Cell Mol. Biol.* 8: 201-208, 1993.
26. Meacham, G. C., Z. Lu, S. King, E. Sorscher, A. Tousson, and D. M. Cyr. The Hdj-2/Hsc70 chaperone pair facilitates early steps in CFTR biogenesis. *EMBO J.* 18: 1492-1505, 1999.
27. Peterec, S. M. K. V. Nichols, D. W. Dynia. C. M. Wilson and I. Gross. Butyrate modulates surfactant protein mRNA in fetal rat lung by altering mRNA transcription and stability. *Am. J. Physiol. Lung Cell. Mol. Physiol.* 267: L9-L15, 1994.
28. Pind, S., J. R. Riordan, and D. B. Williams. Participation of the endoplasmic reticulum chaperone calnexin (p88, IP90) in the biogenesis of the cystic fibrosis transmembrane conductance regulator. *J. Biol. Chem.* 269: 12784-12788, 1994.
29. Rothman, J. E., and S. L. Schmid. Enzymatic recycling of clathrin from coated vesicles. *Cell* 46: 5-9, 1986.
30. Rubenstein, R. C., M. E. Egan, and P. L. Zeitlin, In vitro pharmacologic restoration of CFTR-mediated chloride transport with sodium 4-phenylbutyrate in cystic fibrosis epithelial cells containing DF508-CFTR, *J. Clin. Invest.* 100: 2457-2465, 1997.
31. Rubenstein, R. C., and P. L. Zeitlin, A pilot clinical trial of oral sodium 4-phenylbutyrate (Buphenyl) in DF508-homozygous cystic fibrosis patients: partial restoration of nasal epithelial CFTR function. *Am. J. Respir. Crit. Care Med.* 157: 484-490, 1998.
32. Sato, S., C. L. Ward, and R. R. Kopito. Cotranslational ubiquitination of cystic fibrosis transmembrane conductance regulator in vitro. *J. Biol. Chem.* 273: 7189-7192, 1998.
33. Sato, S., C. L. Ward, M. E. Krouse, J. J. Wine, and R. R. Kopito. Glycerol reverses the misfolding phenotype of the mot common cystic fibrosis mutation, *J. Biol. Chem.* 271: 635-638, 1996.
34. Strickland, E. H., B.-H. Qu, L. Millen, and P. J. Thomas. The molecular chaperone Hsc70 assists in the in vitro folding of the N-terminal nucleotide-binding domain of the cystic fibrosis trans-membrane conductance regulator. *J. Biol. Chem.* 272: 25421-25424, 1997.
35. Ward, C. L., and R. R. Kopito. Intracellular turnover of cystic fibrosis transmembrane conductance regulator. Inefficient processing and rapid degradation of wild-type and mutant proteins. *J. Biol. Chem.* 269: 25710-25718, 1994.
36. Ward, C. L., S. Omura, and R. R. Kopito. Degradation of CFTR by the ubiquitin-proteasome pathway. *Cell* 83: 121-127, 1995.
37. Yang, Y., S. Janich, J. A. Cohn, and J. M. Wilson. The common variant of cystic fibrosis transmembrane conductance regulator is recognized by hsp70 and degraded in a pre-Golgi nonlysosomal compartment. *Proc. Natl. Acad. Sci. USA* 90: 9480-9484, 1993.
38. Zeitlin, P. L., L. Lu, J. Rhim, G. Cutting, G. Stetten, K. A. Kieffer, R. Craig, and W. B. Guggino. A cystic fibrosis bronchial epthelial cell line: immortalization by adeno-12-SV40 infection. *Am. J. Respir. Cell Mol. Biol.* 4: 313-319, 1991.

The following Examples demonstrate that a specific phenyl alkenoic acid, i.e., 4-Phenyl-Δ3-transbutenoic acid, restores the normal biosynthetic trafficking of the ΔF508 protein in CF, and therefore, may be useful as a treatment for disorders or conditions impacted by undesired protein expression such as CF. Without wishing to be bound to any theory, it is believed 4-Phenyl-Δ3-transbutenoic acid words by down regulating Hsc70 which is involved in the degradation of the ΔF508 protein. In addition, it is further believed that the ΔF508 protein acts by inhibiting histone descetylation leading to increased expression of other chloride channels.

4-PBA has been approved by the FDA for the treatment of certain urea cycle disorders. However, the data provided by Examples 4-12 show, among other things, that 4-Phenyl-Δ3-transbutenoic acid is much more effective at lower concentrations.

EXAMPLE 4

Figure 8:
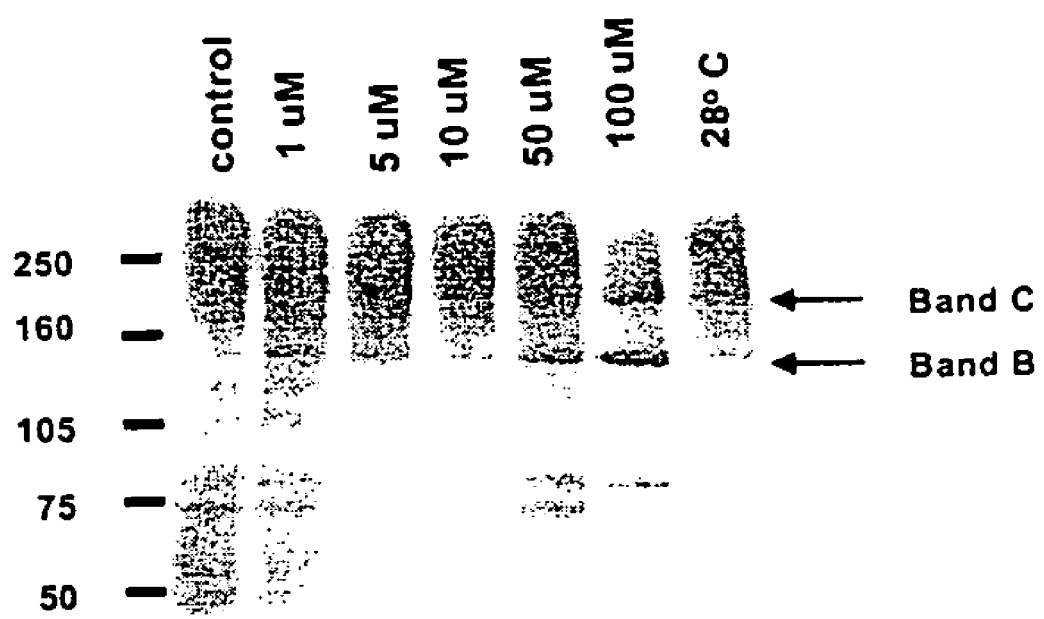
FIG. 8 is a representation of a Western blot showing expression of CFTR in the presence of mM 4-phenyl-Δ3-transbutenoic acid.

4-phenyl-Δ3-transbutenoic Acid Mediated Up-regulation of Band C CFTR in IB3-1 Cells As shown in FIG. 8, IB3-1 (ΔF508/W1282X) cells were exposed to increasing concentrations of the test compounds from 1 μM to 100 μM for 48 hr. CFTR was immunoprecipitated and phosphorylated as described in the Methods. Lane 1 shows control, untreated cells at standard cell culture conditions. Band B CFTR is barely visible consistent with low level ΔF508 expression. The positive control condition, untreated cells grown at 28° C., is in lane 7. Band C has been induced and Band B is relatively depleted consistent with an effect of low temperature on protein trafficking. Lanes 2-6 show a dose-dependent induction of Band C as well as an induction of Band B and total CFTR. This is consistent with an effect on protein production and on protein trafficking.

EXAMPLE 5

Figure 9A:
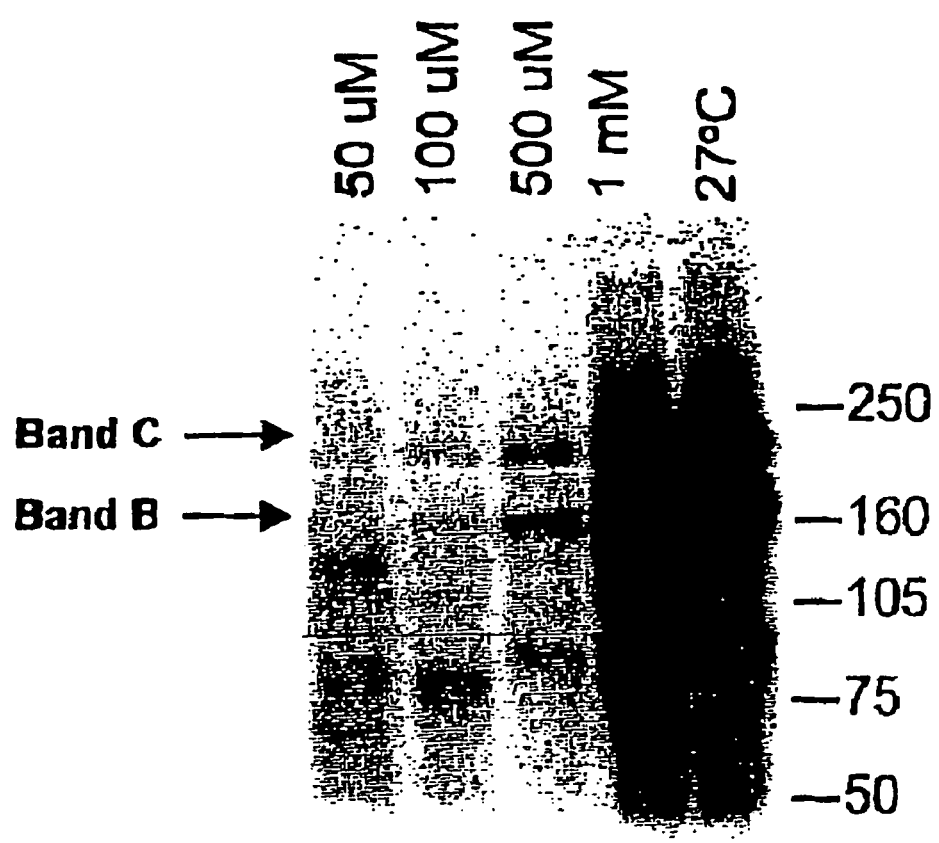
FIGS. 9A and 9B are representations of Western blots showing: 9A. induction of CFTR biosynthesis and processing by a butyrate pro-drug and 9B. 4-phenyl-Δ3-transbutenoic acid up-regulation of of band C in CFTR (IB3-1 cells).
Figure 9B:
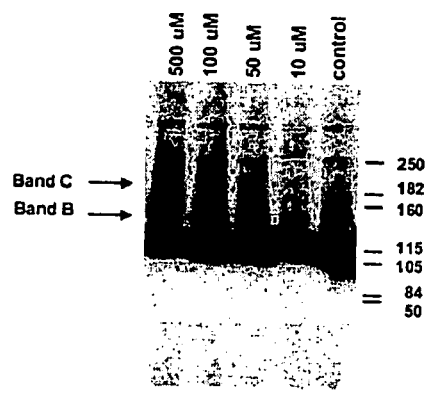

4-phenyl-Δ3-transbutenoic Acid Mediated Up-regulation of Band C CFTR in IB3-1 Cells Shown in FIGS. 9A and 9B are independent experiments performed as described above. Now the control cells are analyzed in lane 5. Lanes 1-4 show decreasing concentrations of the test compound. Again these results show a dose-dependent induction of bands B and C consistent with an increase in CFTR production and protein folding.

EXAMPLE 6

Figure 10A:
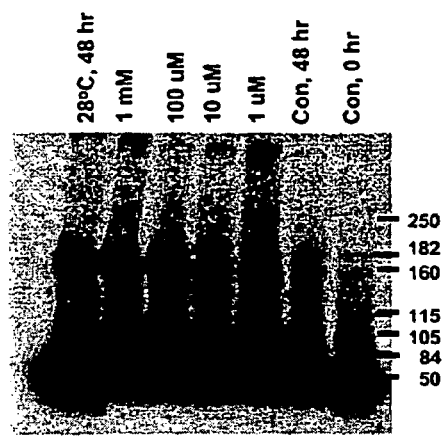
FIGS. 10A and 10B are representations of Western blots showing 4-phenyl-Δ3-transbutenoic acid mediated up-regulation of CFTR in primary cystic fibrosis bronchial epithelial cells.
Figure 10B:
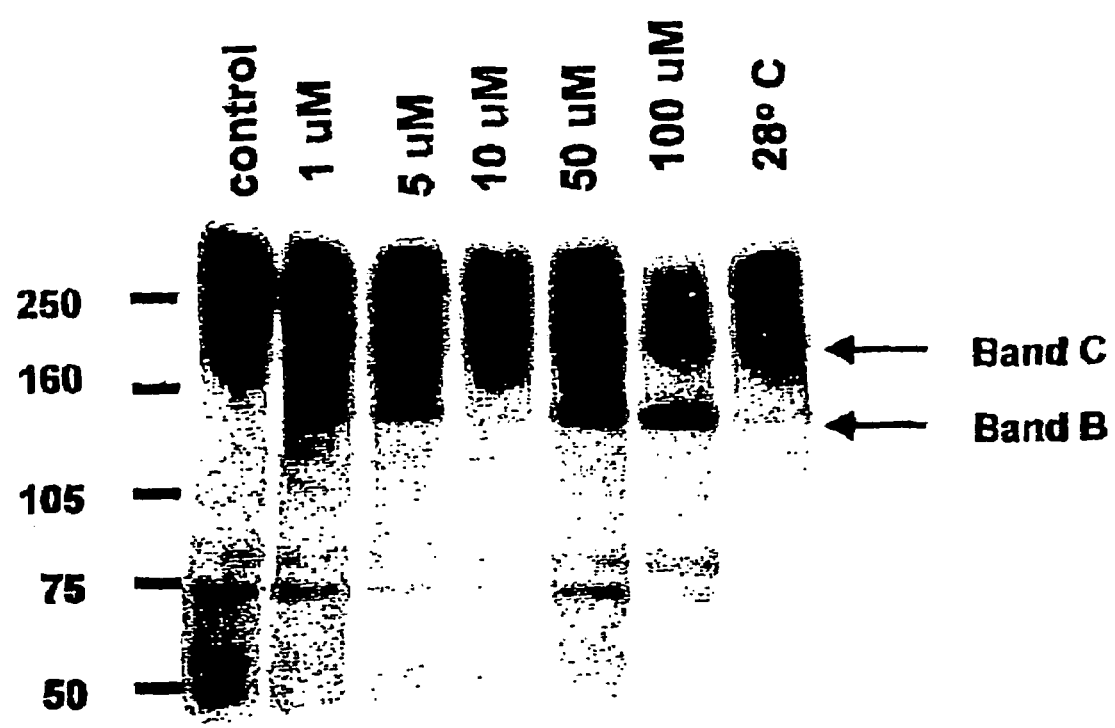

4-phenyl-Δ3-transbutenoic Acid Mediated Up-regulation of Band C CFTR in Primary Cystic Fibrosis Bronchial epithelial Cells Shown in FIGS. 10A and 10B are results of CF bronchial epithelial cells were harvested from the discarded lungs of a CF patient who underwent therapeutic lung transplant. The genotype is homozygous ΔF508. The methods are as described above. Control cells grown in standard conditions for 0 or 48 hrs are in lanes 6 and 7. Bands B and C are barely detectable. The positive control condition, 28° C. is in lane 1 and shows up-regulations of both bands B and C. The test compound in doses from 1 μM to 1 mM for 48 hr is shown in decreasing order in lanes 2-5. The primary patient-derived cells are much more sensitive to the effects and show dramatic induction of bands B and C by 1 μM with maximum induction by 1 mM. These results confirm activity of this compound in primary and immortalized CF airway epithelial cells.

EXAMPLE 7

4-phenyl-Δ3-transbutenoic Acid Mediates Down-regulation of Hsc70 in the Primary CF Cells Studied in FIG. 9

Figure 11:
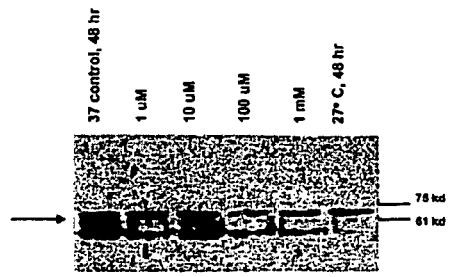
FIG. 11 is a representation of a Western blot showing effect of 4-phenyl-Δ3-transbutenoic acid on hsc70 in primary CF bronchial epithelia. The phenotype is ΔF508/ΔF5058.

Shown in FIG. 11 is an experiment in which cells were exposed to control or test conditions or study drug for 48 hrs and then analyzed by immunoblotting for Hsc70, a 70 kD heat shock chaperone protein. This semi-quantitative blot demonstrates at least a 50% reduction in Hsc70 at 100 μM and 1 mM concentrations (lanes 4 and 5). Hsc70 is not as dramatically down regulated by growth at 27° C.

EXAMPLE 9

Figure 12:
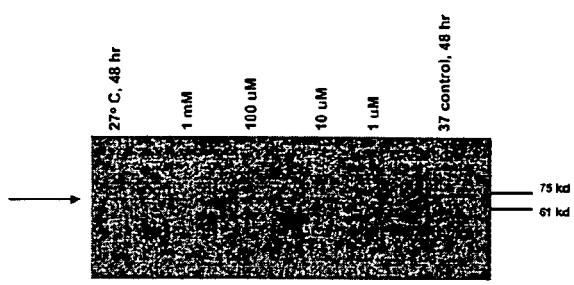
FIG. 12 is a representation of a Western blot showing effect of 4-phenyl-Δ3-transbutenoic acid on hsc70 in the primary CF bronchial epithelia.

4-phenyl-Δ3-transbutenoic Acid Mediates Downregulation of Hsc70 in the Primary CF Cells Studied in FIGS. 9 and 10A Shown in FIG. 12 is an experiment performed along lines as shown in FIG. 10A in the same primary cell line. Hsc70 under control conditions is strongly visible in lane 6. Study drug at 1 μM or higher, and low temperature, are associated with more than 50% reduction in Hsc70.

EXAMPLE 10

Time Course of 4-phenyl-Δ3-transbutenoic Ccid-mediated Up-regulation of Band C

Figure 13:
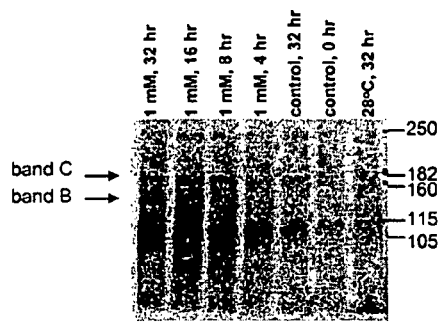
FIG. 13 is a representation of a Western blot showing a time course of 4-phenyl-Δ3-transbutenoic acid up-regulation of band C.

As shown in FIG. 13, IB3-1 cells were exposed to the test conditions and 1 mM study drug for the indicated periods of time. CFTR was detected by immunoprecipitation and phosphorylation. Control cells at 0 and 32 hrs have barely visible CFTR bands B and C. Exposure to low temperature induces band C. 1 mM 4-phenyl-Δ3-transbutenoic acid begins to induce band C and 4 hr and appears maximal by 16 hrs.

EXAMPLE 11

Figure 14:
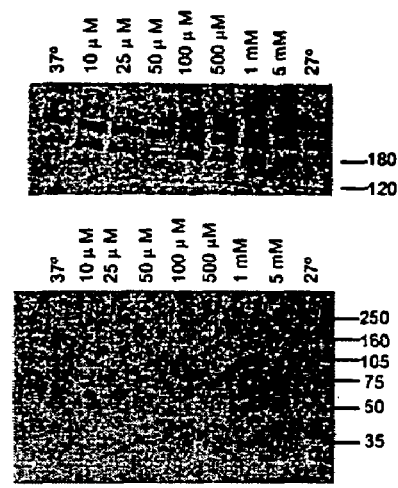
FIG. 14 is a representation of a Western blot showing induction of CFTR band C and of Hsp70 chaperone protein by 4-phenylbutyrate in IB3-1 cells.

Induction of CFTR Band C and of Hsp70 Chaperone Protein by 4-phenylbutyrate in IB3-1 Cells As shown in FIG. 14, IB3-1 cells were exposed to increasing concentrations of 4-phenylbutyrate and then immunoblotted for CFTR with anti-CFTR antibody 181 (upper panel) or for Hsp70 (lower panel). Control cells at 37° C. show band B CFTR, but virtually undetectable band C CFTR. These cells as expected show very little Hsp70, the heat shock inducible chaperone. At 27° C., a lower temperature, there is very little Hsp70 as expected, but as expected, there has been induction of band C CFTR. 4-Phenylbutyrate induces Hsp70 in a dose-dependent manner and also promotes appearance of band C CFTR.

EXAMPLE 12

Overexpression of Hsp70 by transient transfection with Hsp70 cDNA induces CFTR in IB3-1 cells.

Figure 15:
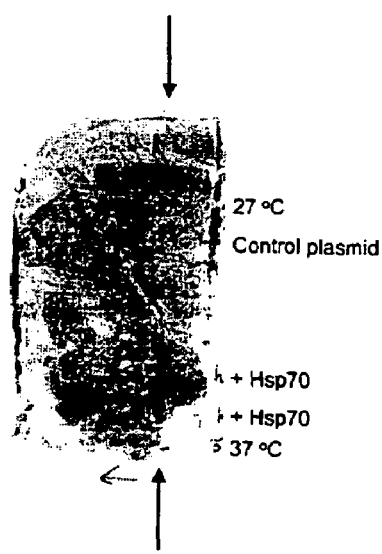
FIG. 15 is a representation of a Western blot showing overexpression of Hsp70 by transient transfection with Hsp70 cDNA.

As shown in FIG. 15, IB3-1 cells were transfected with Hsp70 or a control plasmid using lipofectamine by standard methodologies. After 48 hrs, the cells were collected and immunoblotted with anti-CFTR antibody 181. The arrows indicate the CFTR, however the mobility is somewhere from 160-180 kD. The induction of Hsp70 is associated with a dramatic overproduction of CFTR as compared to control plasmid transfection at 37° C. or growth at 27° C.

EXAMPLE 13

Assay for Determining Nasal Potential Differences in Normal and CF Patients using 4-PBA Standard methods for detecting and quantifying electrical potentials from nasal epithelia have been reported. See e.g., Zeitlin, P. L. (2000) in *Mol. Therapy* 1: 1; Noone, P. G. et al. (2000) in *Mol. Therapy* 1: 105-114; Caplen, J. J. et al. (1995) *Nat. Med.* 1: 39-46; Middleton, P. G. (1994) in *Eur. Respir.* 7: 2050-2056; the disclosures of which are hereby incorporated by reference.

Using these and related approaches, nasal potential difference patterns from normal and CF patients were analyzed. See FIG. 16A.

Figure 16A:
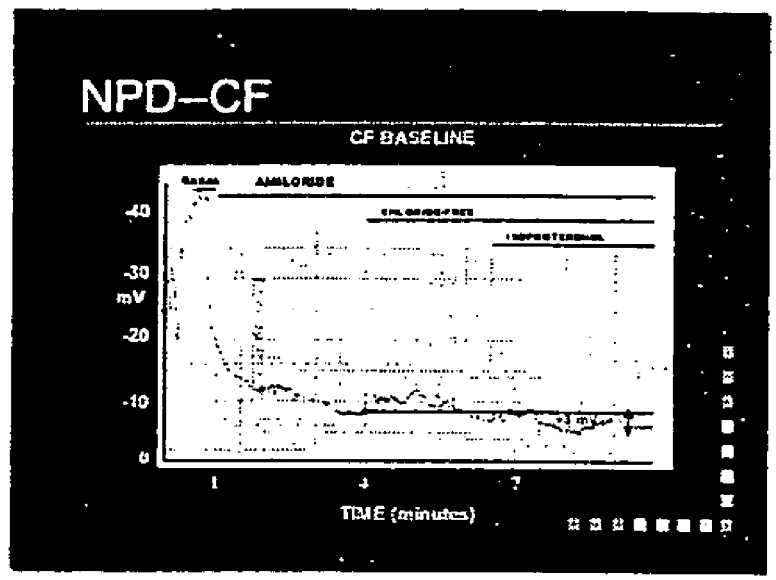
FIGS. 16A-D are graphs showing nasal potential difference patterns in normal subjects (FIGS. 16B) and CF patients (FIGS. 16A, 16C-D). Administration of 4-phenylbutyrate increases presence of functional CFTR in nasal epithelia (FIGS. 16C-D).

Briefly, FIG. 16A shows a nasal potential difference pattern from an individual with cystic fibrosis. The methodology employed involves superfusion of the inferior turbinate with Ringer's solution and measurement of the electrical potential with reference to a subcutaneous electrode. This CF pattern shows a typical hyperpolarization, large amiloride inhibition, and minimal repolarization to low chloride or isoproterenol maneuvers.

Figure 16B:
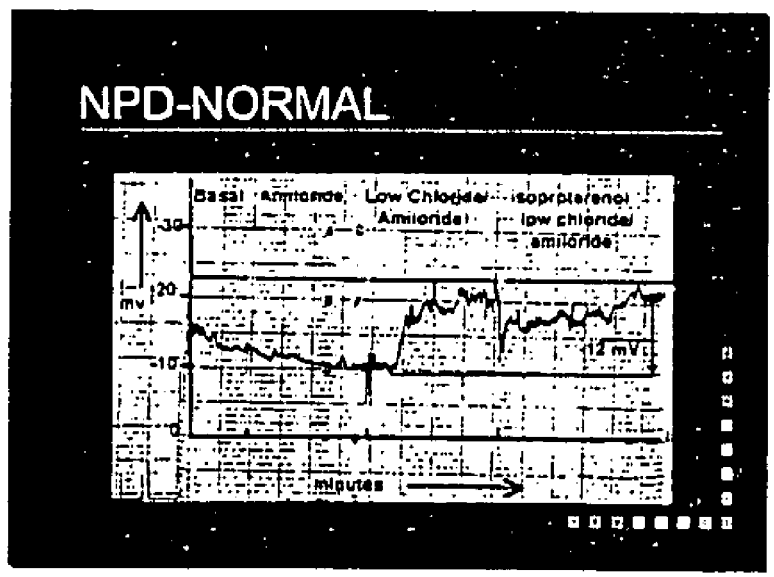

FIG. 16B shows a nasal potential difference pattern in an non-CF individual. The baseline potential is less polarized than in CF. The amiloride inhibition is much lower. The low chloride and isoproterenol exposure induce a sizeable repolarization.

Figure 16C:
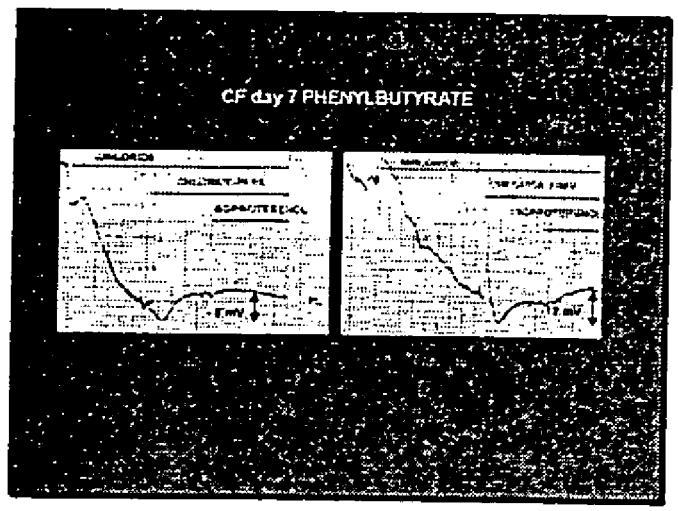

FIG. 16C shows a nasal potential difference pattern of a patient with CF (deltaF508 homozygous) who has taken 20 gm 4-phenylbutyrate daily for 7 days. The low chloride/isoproterenol exposures induce chloride transport. This is consistent with the presence of a functional CFTR in the nasal epithelial cell surface.

Figure 16D:
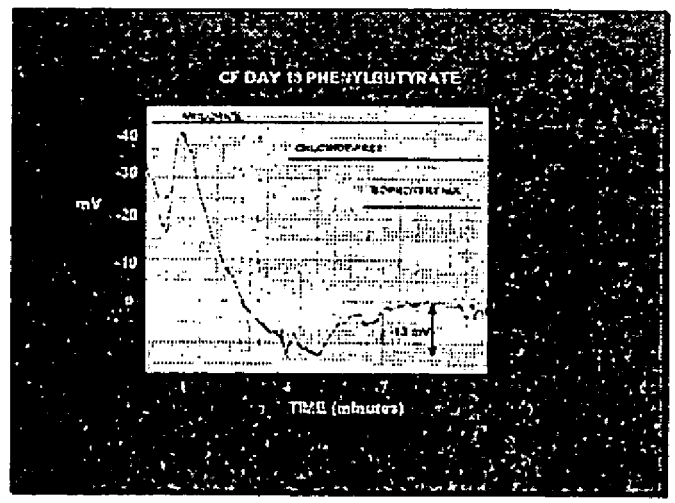

FIG. 16D the same individual as in FIG. 16D after 18 days on 4-phenylbutyrate. The low chloride/isoproterenol exposure continues to sustain chloride transport.

The foregoing experiments using human nasal epithelia can be readily repeated using any one or more of the carbocyclic aryl compounds of this invention, preferably a phenyl alkenoic acid, and more preferably 4-phenyl-Δ3-transbutenoic acid; or a pharmaceutically acceptable salt thereof. Preferred compounds will exhibit comparable activity with 4-PBA. More preferred compounds with exhibit better activity by at least about 2 fold in this assay.

All reference disclosed in this application are incorporated are incorporated herein by reference.

While the invention has been described with reference to specific embodiments, modifications and variations of the invention may be constructed without departing from the scope of the invention, which is defined in the following claims.

What is claimed is:

1. A method of treating a disease associated with incorrect protein expression of a transmembrane protein in a mammal in need thereof, comprising:

administering to the mammal a therapeutical effective amounts of 4-phenyl-Δ3-transbutenoic acid or a pharmaceutically acceptable salt thereof, wherein the disease is cystic fibrosis and the transmembrane protein is cystic fibrosis transmembrane regulator.

2. The method of claim 1 wherein the mammal is identified as suffering from cystic fibrosis and the compound is administrated to the identified mammal.

3. The method of claim 1 wherein the mammal is human.

* * * * *